United States Patent
Fernandez et al.

[11] Patent Number: 5,811,124
[45] Date of Patent: Sep. 22, 1998

[54] MICROPARTICLES WITH HIGH DRUG LOADING

[75] Inventors: Julio M. Fernandez, Rochester; Mark B. Knudson, Shoreview, both of Minn.

[73] Assignee: Mayo Foundation for Medical Education and Research, Rochester, Minn.

[21] Appl. No.: 389,157

[22] Filed: Feb. 15, 1995

Related U.S. Application Data

[60] Division of Ser. No. 250,464, May 27, 1994, which is a continuation-in-part of Ser. No. 17,681, filed as PCT/US94/01924 Feb. 10, 1994, abandoned.

[51] Int. Cl.[6] ................................................ A61K 9/16
[52] U.S. Cl. .................... 424/489; 424/484; 424/485; 424/486; 424/487; 424/488; 424/499; 424/500; 424/501
[58] Field of Search .................... 424/489, 499, 424/500, 501, 484–488; 264/4.1–4.3

[56] References Cited

FOREIGN PATENT DOCUMENTS

0426463 A2   5/1991   European Pat. Off. .

OTHER PUBLICATIONS

Kwan Nature 354, p. 291 Nov. 1991.
Fernandez Biophys. J. 59 p. 1022 May 1991.
Verdugo Biorheology 24, p. 625 1987.
Curran J. Gen. Physiol. 98, p. 771, Oct. 1991.
Hoffman Artifical Organs 16(1) p. 43 1992.
J.T. Science 259 p. 893 Feb. 1993.

*Primary Examiner*—Gollamudi S. Kishore
*Attorney, Agent, or Firm*—Dehlinger & Associates

[57] ABSTRACT

An microparticle composition and its method of use in drug delivery and diagnostic applications are disclosed. Also disclosed are methods of storing and administering drug compounds at high concentration in condensed-phase microparticles.

6 Claims, 12 Drawing Sheets

↓ UV

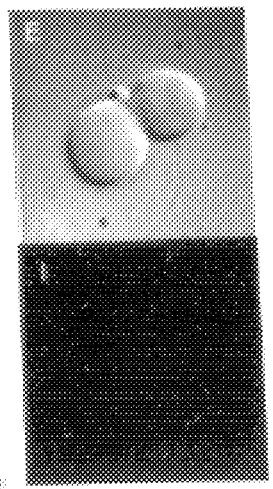
Fig. 8A
Fig. 8B
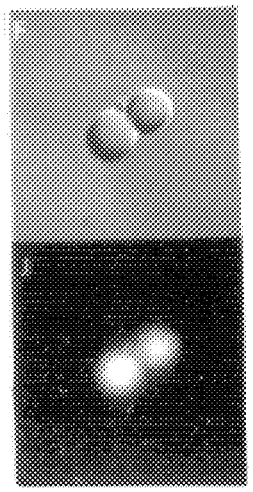
Fig. 8C
Fig. 8D
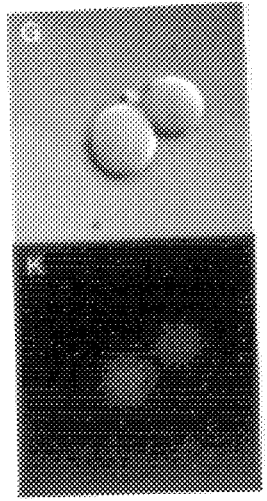
Fig. 8E
Fig. 8F
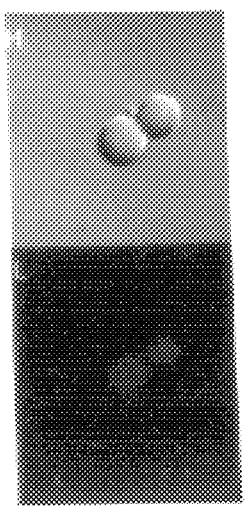
Fig. 8G
Fig. 8H

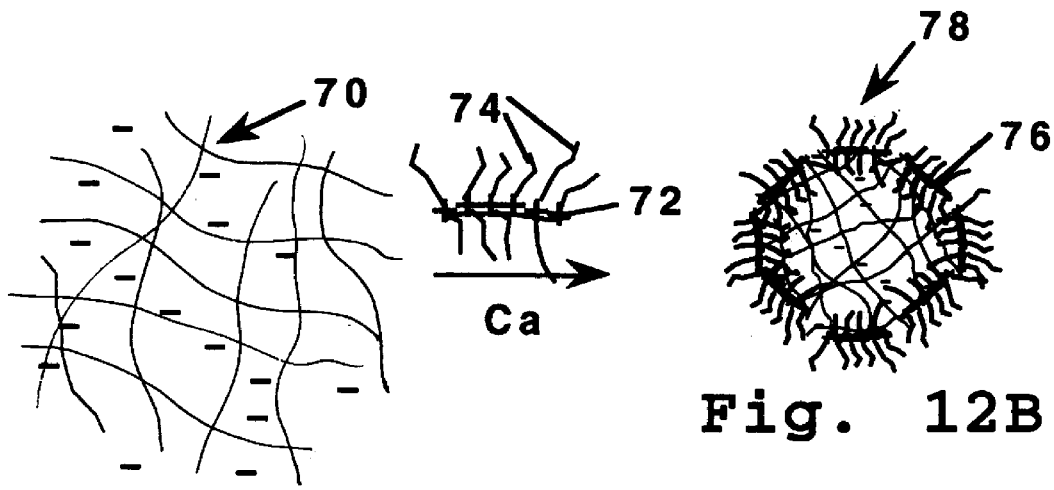
Fig. 12A
Fig. 12B
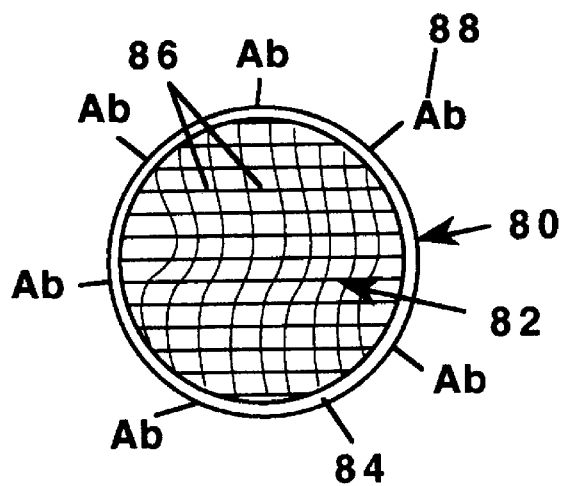
Fig. 13

MICROPARTICLES WITH HIGH DRUG LOADING

This application is a division of U.S. patent application Ser. No. 08/250,464, filed May 27, 1994, which is a continuation-in-part of U.S. patent application Ser. No. 08/017,681, filed Feb. 12, 1993 now abandoned, and claims priority of PCT application PCT/US94/01924 for "Condensed-Phase Microparticle Composition and Method," filed Feb. 10, 1994.

1. Field of the Invention

The present invention relates to condensed-phase polymer-matrix microparticles and their uses a drug delivery, drug storage, and in diagnostic applications.

2. References

Antonietti, M., et al., *Macromolecules,* 18:1162 (1985).
Arshady, R., *Biomaterials* 14(1):5–20 (1993).
Cadan, F., et al., *J. Poly Sci.,* Part A, 23:193 (1985).
Hosaka, S., et al., *Immunological Communications* 12(5):509–517 (1983).
Huang, Y., et al., *Makromol. Chem.,* 186:273 (1985).
Kamei, S., et al., *J. Polymer Sci.: Part A: Polymer Chem.* 24:3109–3116 (1986).
Kawaguchi, H., et al., *Polymer J.* 23(8):955–962 (1991).
Kawaguchi, H., et al., *Colloid and Polymer Sci.* 270(1):53 (1992).
Kawaguchi, H., et al., *Polymer Int.* 30:225–231 (1993).
Kreuter, J., in *Microcapsules and Nanoparticles in Medicine and Pharmacy,* CRC Press, Boca Raton Fl. (1992).
Margel, S., et al., *J. Cell Sci.* 56:157–175 (1982).
Okubo, M., et al., in "Production of Multihollow Polymer Particles by Stewise Alkali-Acid Method" in *Polymer Latexes* (Daniels, E. S., et al., eds.) American Chemical Society, Washington D.C. (1992).
Okubo, M., and Nakagawa, T., *Collid Polym. Sci.* 270:853–858 (1992).
Pelton, R. H., and Chibante, P., *Colloids and Surfaces* 20:247–256 (1986).
Pelton, R. H., *J. Polym. Sci.: Part A: Polym. Chem.* 26:9–18 (1988).
Szoka, F., et al., *Ann Rev Biophys Bioeng,* 9:467 (1980).
Szoka, F., et al., *Proc Nat Acad Sci, USA* 75:4194 (1978).
Tai, E. F., *J Poly Sci.,* Part A, 24:567 (1986).
Tanaka, H., et al., *Biotech. and Bioeng.* 26:53–58 (1984).
Vanderhoff, M. S., et al., *Polym. Matr Sci Eng.,* 54:587 (1986)
Wong. S. S., *Chemistry of Protein Conjugation and Crosslinking,* CRC Press, 1991.
Yui, N., et al., *J. Controlled Rel.* 22:105–116 (1992).

3. Background of the Invention

The use of synthetic polymers in drug delivery devices has focused on "smart polymers" a term ascribed to polymers which form gels that have the ability to expand or contract in response to a specific stimulus, such as light, temperature or pH. Typically, such polymers will precipitate in solution or collapse with concomitant expulsion of gel pore contents. In some cases, these processes are reversible.

Synthetic polymers may be based on a number of types of monomeric units, including vinyl monomers, N-alkyl substituted acrylamides and the like. Copolymers have also been utilized in an attempt to combine or modulate the stimulus responsive properties of one or more known smart polymers.

4. Summary of the Invention

The present invention includes, in one aspect, a particle composition for rapid release of a compound, when the composition is exposed to a selected target condition related to pH, temperature, or the presence of a selected ligand. The composition includes encapsulated, condensed-phase microparticles having an average size in a selected size range between 0.05 and 5 microns.

Each microparticle is composed of a condensed-phase matrix of crosslinked polyionic polymer filaments, and is capable of decondensing to an expanded phase when selected multivalent counterions also present within the matrix are replaced by monovalent counterions. The compound to be delivered is entrapped in the condensed-phase microparticle. The condensed-phase microparticle and entrapped drug are encapsulated within a lipid bilayer membrane. LcocaLized disruption of the lipid membrane, and influx of monovalent counterions into the polymer matrix, in response to the selected target conditions, causes a cascade effect involving matrix swelling and further membrane disruption, resulting in rapid compound release from the particles.

In one general embodiment, the composition is designed for use as a drug-delivery composition. Here the microparticles have an average size in a selected size range preferably between 0.05 and 0.5 microns, the compound is a therapeutic compound, and the lipid membrane is effective to allow influx of external counterions into the microparticle matrix when exposed to a selected condition in vivo.

In a more specific embodiment, the polymer filaments forming the microparticle matrix are sulfated, sulfonated, carboxylated, or polyphosphated polyanionic polymers, preferably comb-polymer glycoprotein filaments, and the multivalent counterion is a multivalent cation.

Also in more specific embodiments, the encapsulated microparticles contain a concentration of solute molecules, including a therapeutic compound, that in the absence of the matrix, would produce hypertonic swelling of the encapsulated microparticle's lipid membrane in a physiological medium. Alternatively, the concentration of therapeutic compound within the encapsulated microparticles is greater than the solubility of the drug in the aqueous medium within the microparticle matrices.

The lipid bilayer membrane may include anti-ligand molecules attached to the outer membrane surface, for binding specifically to ligand antigen or antibody molecules present at an in vivo site, for producing complement-mediated lysis at the selected in vivo site. For use in delivering a drug to a site that can be heated to an elevated temperature above normal body temperature, the encapsulated microparticles' lipid membranes are formed of lipids having a phase transition temperature between the normal body temperature and the elevated temperature.

In a second general embodiment, the composition is used as a diagnostic assay reagent, such as a homogeneous assay reagent. Here the lipid membrane contains surface-bound anti-ligand molecules effective to bind specifically and with high affinity to a selected analyte ligand molecule, and the entrapped compound is a detectable reporter compound.

Binding of an analyte ligand to the anti-ligand molecules, in the presence of complement, causes membrane lysis, with rapid release of entrapped reporter compound.

In another aspect, the invention includes a method delivering a therapeutic compound to an in vivo target site having a selected pH, temperature, or binding-molecule characteristic, by administering an encapsulated microparticle composition of the type described above to a subject in need of the compound. The administered composition is effective to produce rapid release of the compound at the target site.

Also disclosed is a method of storing a charged compound, typically one that is unstable on storage. The method includes infusing the compound into polymer microparticles having selected sizes in the 0.02 to 50 micron size range, preferably 0.05 to 5μ, where each particle is composed of a decondensed-phase matrix of crosslinked polyionic polymer filaments, and is capable of contracting to a condensed phase under selected ionic conditions requiring the presence of multivalent counterions.

After the compound has infused into the decondensed-phase microparticles, multivalent counterions are added to the medium at a concentration effective to fully condense the microparticles, forming an aqueous suspension of condensed-phase microparticles having entrapped compound. The microparticles are preferably stored in an aqueous suspension or in a particle, partially dehydrated form.

The entrapped compound, which has the same charge as the counterion, may be loaded into the microparticles at high concentration due to the high coefficient of partitioning of the compound into the charged matrix. The method is useful, for example, for storing polypeptides at a high concentration, without loss of activity due to denaturation by lyophilization, or proteolysis or other solution-related degradation.

The condensed-phase particles may be used for rapid compound release in therapeutic applications, or for rapid release of chemical-reagent compounds, such as diagnostic reagents, in chemical-reaction applications. When used in therapeutic applications, the condensed-phase microparticles have preferred sizes in the size range 0.05 to 0.5 μm.

In still another aspect, the invention includes a compound-release composition comprising a suspension of condensed-phase microparticles having average sizes in a selected size range preferably between 0.05 and 50 microns. Each microparticle is composed of (i) a matrix of crosslinked polyionic polymer filaments capable of swelling from a condensed phase to an expanded, decondensed phase or state, when the matrix is exposed to monovalent counterions, (ii) small molecules entrapped in the microparticle matrix, with such in its condensed phase, and (iii) polyvalent counterions effective to retard the release of the small molecules from the microparticles, when the microparticles are exposed to monovalent counterions.

The polyvalent counterions may be confined to an outer shell region of the condensed-phase matrix, infused throughout the matrix, or distributed within the matrix according to the polymer-molecule size.

The polymer filaments forming the microparticle matrix in one embodiment are sulfated, sulfonated, carboxylated, or polyphosphated polyanionic polymers, and the polyvalent counterions are polycationic polymer molecules, preferably polypeptides with a net side chain charge.

In one general embodiment, the composition is used for parenteral administration of an entrapped therapeutic compound, with the condensed-state microparticles hanging sizes in the range 0.05 to 0.5 μm. The composition may be used for delivering a charged therapeutic peptide, which can serve as a polyvalent species in the composition. Alternatively, the therapeutic compound may be a small therapeutic molecule which is entrapped in the matrix, with such in its condensed form. The therapeutic compound may be present at a concentration that is substantially greater than the water solubility of the compound in the suspension. The compound preferably has the same charge as the counterion.

These and other objects and features of the invention will become more fully apparent when the following detailed description of the invention is read in conjunction with the accompanying drawings.

BRIEF DESCRIPTION OF THE DRAWINGS

FIGS. 8A–8H are light photomicrographs (8A, 8C, BE, and 8G) and fluorescent micrographs (8B, 8D, 8F, 8H) of microparticles (i) before particle condensation (8A and 8B); (ii) after microparticle loading with fluorescent histamine (8C and 8D); (iii) after decondensing the fluorescent-loaded particle with Na$^+$-containing medium (8E and 8F); and after a second particle condensation with unlabeled histamine (8G and 8H);

FIGS. 12A and 12B show a method of attaching polyethleneglycol polymer chains to the exterior surface of a microparticle;

FIG. 13 shows an encapsulated microparticle for use in a compound-release composition formed in accordance with another aspect of the invention;

DETAILED DESCRIPTION OF THE INVENTION

I. Definitions

Figure 1:
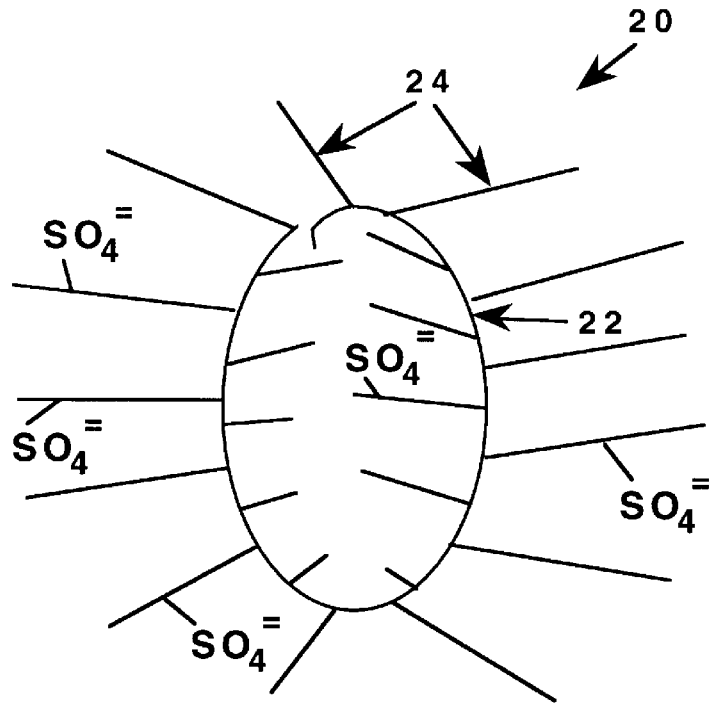
FIG. 1 shows a generalized structure of a sulfated comb-polymer glycoprotein used in forming a polymer-matrix microparticle in accordance with the invention.

As used herein, the terms below have the following definitions unless indicated otherwise.

"Polyionic polymers" or "polyionic polymer filaments" are polymers containing multiple charged subunits (subunits containing at least 1 negative or positive charge at a selected pH between about 4–10), and having a net negative (polyanionic) or net positive (polycationic) charge at the selected pH.

"Polyanionic polymers" or "polyanionic polymer filaments" are polyionic polymers in which the charged subunits are ionizable, negatively charged subunits, typically sulfate, sulfonate, or carboxylate, or phosphate groups. Such polyanionic polymers or polymers filaments are also referred to herein as "sulfated, sulfonated, carboxylated, or phosphated" polymers or polymer filaments, respectively.

"Polycationic polymers" or "polycationic polymer filaments" are polyionic polymers in which the charged subunits are ionizable, positively charged subunits, typically primary, secondary, or tertiary amine groups, or in which the charged subunits contain quaternary amine groups.

"Polyionic hydrophilic polymers" are polyionic polymers which are soluble in an aqueous solution, at a selected pH between about 3–10, preferably having a partition coefficient, expressed as log n-octanol/water, of less than zero.

"Comb polymers" or "comb-polymer filaments" are polymer filaments composed of a polymeric backbone chain and a plurality of polymer side chains attached to the backbone polymer at spaced positions along the backbone chain, and radiating outwardly from the backbone chain.

A "comb-polymer glycoprotein" refers to a comb polymer having a polypeptide backbone chain to which is attached, at spaced positions along the polypeptide chain, a plurality of anionic polysaccharide side chains.

A "sulfonated, sulfonated, carboxylated, or phosphated comb-polymer glycoprotein" refers to a polyanionic comb-polymer glycoprotein in which the polysaccharide side chains carry sulfate, sulfonyl, carboxyl, or phosphate groups, respectively, at one or more sugar residues.

"Glycosaminoglycans" consist of disaccharide repeating units containing a derivative of an amino sugar (glucosamine or galactosamine) where at least one of the sugars in the disaccharide contains a carboxylate or sulfate group. Exemplary glycosaminoglycans include hyaluronate, chondroitin sulfate, keratin sulfate, heparin sulfate and heparin.

"Proteoglycan" refers to a polypeptide backbone to which is attached multiple anionic heteropolysaccharide sidechains which are generally glycosaminoglycans.

A "crosslinked polymer matrix" is a matrix of polymer filaments in which the filaments are crosslinked by covalent crosslinking between and/or among filaments by bifunctional or polyfunctional crosslinking agents, or crosslinked by ionic bonds between ionic groups on the polymer filaments and multivalent oppositely charged crosslinking species.

A "multivalent solute species" is a divalent or multivalent anionic or cationic solute species.

"Polyvalent counterions" are multivalent solute species each containing at least 3 charged groups (of the same charge), typically amine or carboxyl charged groups. Included in this definition are polypeptides, such as polylysine or polyaspartate, or proteins containing a charged side chain, and nonpeptide polymers, such as polyquaternary amines, having a high density of positively or negatively charged monomer units.

A "monovalent counterion", a "divalent counterion", or a "multivalent counterion" is a monovalent, divalent, or multivalent ionic species, respectively, whose charge is opposite to that of the charge of the polymer matrix. In a matrix formed of polyanionic filaments, the counterion is a cationic species, and in a matrix formed of polycationic filaments, the counterion is an anionic species.

"Polyvalent counterions" are multivalent counterions containing at least 3 charged groups (of the same charge), typically amine or carboxyl charged groups. Included in this definition are polypeptides, such as polylysine or polyaspartate, or proteins containing a charged side chains, and nonpeptide polymers, such as polyquaternary amines, having a high density of positively or negatively charged monomer units.

"Microparticles" refer to particles which are formed of a crosslinked polyionic polymer matrix, and which have condensed-state sizes in the range between about 0.05 to 50 $\mu$m ($\mu$meter), preferably 0.05 to 5 $\mu$m ($\mu$meter).

"Condensed-phase microparticles" or "condensed-state microparticles" refers to microparticles in a condensed or collapsed phase. The matrix in a collapsed phase preferably contains less than about 30 percent by volume water.

"Decondensed-phase microparticles" or "decondensed-state microparticles" refers to microparticles in an expanded decondensed phase in which the particle matrix is open to diffusion of small molecules into and out of the matrix.

The "effective concentration" of a compound in a condensed-phase microparticle, expressed in mM, is the concentration of the compound expressed as moles compound/volume condensed-phase microparticle, calculated from the known size of the condensed-phase particle.

II. Polymer-Matrix Microparticles

This section describes the preparation and properties of polymer-matrix microparticles used in various aspects of the invention.

The microparticles are composed of crosslinked polyionic filaments, and preferably a crosslinked network of polyanionic filaments, such as sulfated, sulfonated, or carboxylated polymers, including comb-polymer glycoproteins. Exemplary polymer filaments, and methods of preparing the crosslinked matrices, either by isolation from biological sources, or by synthetic means, will be described below.

According to an important aspect of the invention, the particles can be cycled rapidly between condensed and decondensed states or phases, by changing the ionic environment of the microparticles. In the condensed phase, the microparticles are relatively dense and opaque, and preferably contain less than about 30 percent by volume water, and preferably less than about 5–15 percent by volume. The condensed-phase microparticles have preferred average sizes in the size range between 0.05 and 50 $\mu$m (micrometer), preferably 0.05 to 10 $\mu$m, and 0.05 to 0.5 $\mu$m for therapeutic uses.

A. Isolation of Microparticles

Microparticles suitable for use in the methods and compositions of the invention may be isolated from one or more suitable biological sources, including cultured cells, as described below. In certain embodiments of the invention, microparticles are isolated as the intact cores of secretory granules. Such granules are typically composed of a membrane surrounding a core of highly charged biopolymers. Proteoglycans, as found in mast cell granules are particularly preferred for forming polymer-matrix microparticles for use in various embodiments of the invention described herein. Glycoproteins, such as form mucous, may also be useful in forming microparticles for certain applications.

Secretory granules can be obtained from mast cells, goblet cells, chromaffin cells and other secretory cells, according to the particular biopolymer and chemical properties required. For example, goblet cell granules contain mucin, a mixture of linear polyanionic glycoproteins, whereas mast cell granules contain heparin proteoglycans, which contain ester sulfate groups. Biopolymers isolated from each of these sources have different characteristics. Mucin-containing granules decondense to form a diffuse gel, while mast cell-derived heparin proteoglycan particles maintain a particulate form following decondensation. Other secretory granule derived materials include, but are not limited to, chromogranin A from chromaffin granules of the adrenal medulla and acidic protein SP-1 from parathyroid granules. In addition, polyanionic chromogranin A-like matrices are present in secretory cells of the thyroid, pancreatic islet cells, sympathetic ganglia, anterior pituitary and gastric antrum.

Preferred isolation techniques for secretory granules from cells include homogenizing the cells with a mechanical homogenizer, treating the cells with detergents, rupturing the cells by sonication, or combinations thereof. The homogenizing or sonicating conditions may leave the granule membranes substantially intact on the granules. Alternatively, cells may be stimulated to release the secretory granules, such as by contact with a releasing agent.

Preferably, to form biological microparticles for use in the invention, the mast-cell membranes will be removed, either during the isolation process, or by detergent means thereafter, as described for mast cell granules in Example 1. After the secretory granules are released from the ruptured cells, the granules are then separated from the cell debris by centrifugation in a density gradient, for example, a sucrose gradient or a metrizamide gradient. Such cell rupturing and centrifugation procedures are well known in the art.

Preferred secretory granules for isolation of polymer-matrix microparticles include mast cell granules. Mast cells can be obtained from the peritoneal cavity of various rodent species. Adult beige mice (bg$^J$/bg$^J$, Jackson Laboratories, Bar Harbor, Me.) are particularly convenient sources of such cells, as described in Example 1. Cells are collected by peritoneal lavage, and the isolated cells are equilibrated in an isosmotic "extracellular" solution. Cells are stimulated to secrete granules, by use of a secretagogue, such as compound 48/80, or by mild sonication, as detailed in Example 1.

These alternative methods of stimulating release of granules from secretory cells result in differences in initial appearance of the granules. Granules released by stimulation with Compound 48/80 decondense rapidly upon release, but can be recondensed to within 5% of original intracellular volume by immersion, for example in a solution containing 50 mM histamine, pH 3. Granules isolated by mild sonication retain an intact granule membrane and their condensed form. Membranes enclosing the granules may then be removed by conventional techniques such as detergent treatment (e.g., Triton X 100) or strong sonication.

Mucin containing secretory granules may be isolated from secretory cells located in the respiratory system called "Goblet" cells. When released from the granules, mucins undergo massive swelling to form a gel in aqueous solution (Verdugo). Mucin particles can be isolated from primary cultures of Goblet cells from rabbit trachea, according to standard methods. Such cultured cells spontaneously degranulate in a manner similar to mast cells. Upon release from the cell, mucin-containing granules swell rapidly for 5–10 sec. The granules generally anneal with each other in the extracellular fluid. The swelling process can be retarded significantly by elevation of calcium content in the extracellular medium (Verdugo).

B. Synthetic Microparticles

Polymer-matrix microparticles having the rapid condensation/decondensation properties described above can also be made synthetically by a variety of methods. The microparticles are made by cross-linking polyionic hydrophilic polymers under conditions which lead to cross-linked matrices in the 0.05 to 50 $\mu$m, preferably 0.05 to 5 $\mu$m particle-size range, when the particles are in their condensed phases.

C. Filament Preparation and Crosslinking

Below are described two general methods for producing polyionic filament components in the microparticles.

1. Prepolymerized ionic polymer filaments.

In one embodiment, the microparticles are prepared by crosslinking existing ionic polymer filaments. Polymer filaments that are suitable include sulfated, sulfonated, carboxylated, or phosphated hydrophilic polymers, in forming negatively charged polymer matrices, and amine-containing hydrophilic polymers, in forming positively charged polymer matrices.

Preferred polyanionic polymer filaments include sulfated proteoglycans, e.g., sulfated heparin, and other sulfated polysaccharides, such as sulfated cellulose or cellulose derivatives, carrageenin and dextran sulfate, mucin, sulfated polypeptides, such as polylysine with sulfated amine groups, and glycopeptides with sulfonate-derivatized saccharide or peptide subunits, and hyaluronic acid.

Figure 2A:
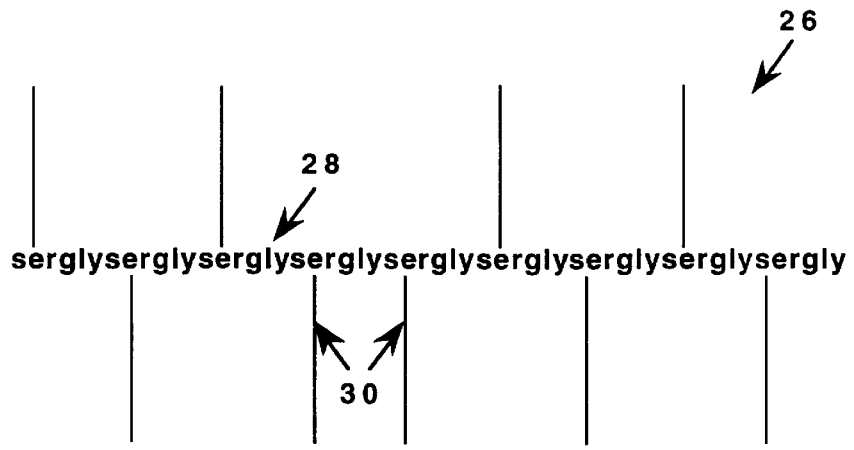
FIGS. 2A and 2B show the backbone structure of a heparin sulfate proteoglycan polymer (FIG. 2A), and the side chain structure of the same polymer (FIG. 2B)

One type of preferred polyanionic polymer filament includes sulfated, sulfonated, carboxylated, or phosphated comb-polymer glycoproteins. The basic structure of this type of polymer is shown in FIG. 1. The polymer, indicated at 20, generally includes a polymeric backbone 22, such as a polypeptide, such as one having repeating subunits, such as repeating amino acid subunits. Attached to the backbone, at attachment points spaced along the backbone, are a plurality of polysaccharide side chains, such as side chains 24. The side chains carry negatively charged sulfate groups, as shown, typically several per chain, but an average of at least about 1 negatively charged group per chain.

Where the backbone polymer contains amino acid residues, the subunit side chains may have a variety of selected chemically reactive groups, such as a hydroxyl, carboxy, or amino groups, by which the side chains of the comb-polymer can be attached to the polymer, such as illustrated for the SER-GLY repeat backbone shown in FIG. 2A.

If the comb-polymer can be prepared de novo, a variety of coupling reaction are available for attaching the aside chains covalently to the backbone polymer. In general, this is done by activating one end of the polysaccharide :side chains, and reacting the activated chains with a backbone under conditions effective to couple the activated chains to corresponding reactive side-chain groups on the polypeptide or other polymer backbone. Coupling reactions suitable for coupling to carboxy, hydroxyl, amino, or sulfhydryl groups are well known.

The percentage of backbone reactive groups, and the relative lengths and stoichiometry of the polymer filament backbone chain and side chains, is preferably such that the comb-polymer preferably includes at least about 80–95% by weight polysaccharide components.

Figure 2B:
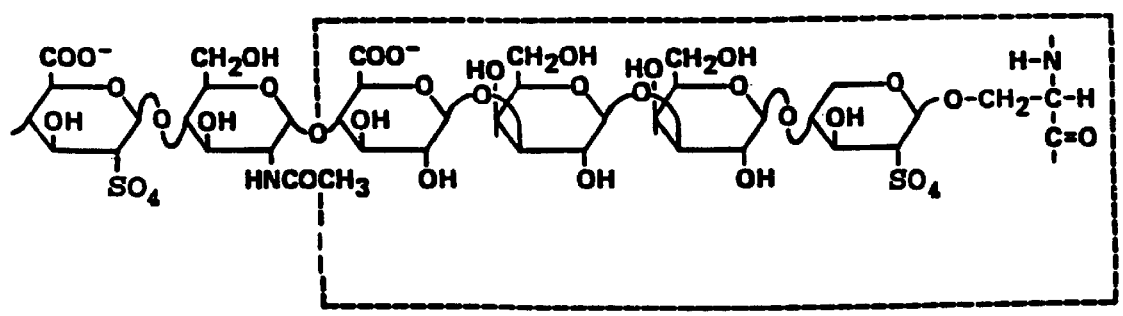

One preferred sulfated comb-polymer glycoprotein is heparin sulfate proteoglycan, whose structure is indicated in FIG. 2A. As seen, the polymer (indicated at 26) has a polypeptide backbone 28 composed of repeating SER-GLY dipeptide subunits, with heparin chains, such as side chains 30, attached to the backbone at some of the SER residues, through the SER hydroxyl group. A portion of a heparin side chain is shown in FIG. 2B.

Proteoglycan polymer filaments of this type may be synthesized following known methods, such as those outlined above. Alternatively, some proteoglycan filaments, such as heparin sulfate proteoglycan, can be obtained by isolation from biological sources.

The preformed filaments may be crosslinked by bifunctional or multifunctional crosslinking agents effective to form intermolecular links between the filaments. In one general embodiment, the crosslinking agent may be a long, hydrophilic polymer chain, such as a polyethyleneglycol (PEG) chain, having activated end groups effective to form covalent linkages to selected reactive groups on the polysaccharide side chains of the polymer filaments.

Figure 3:
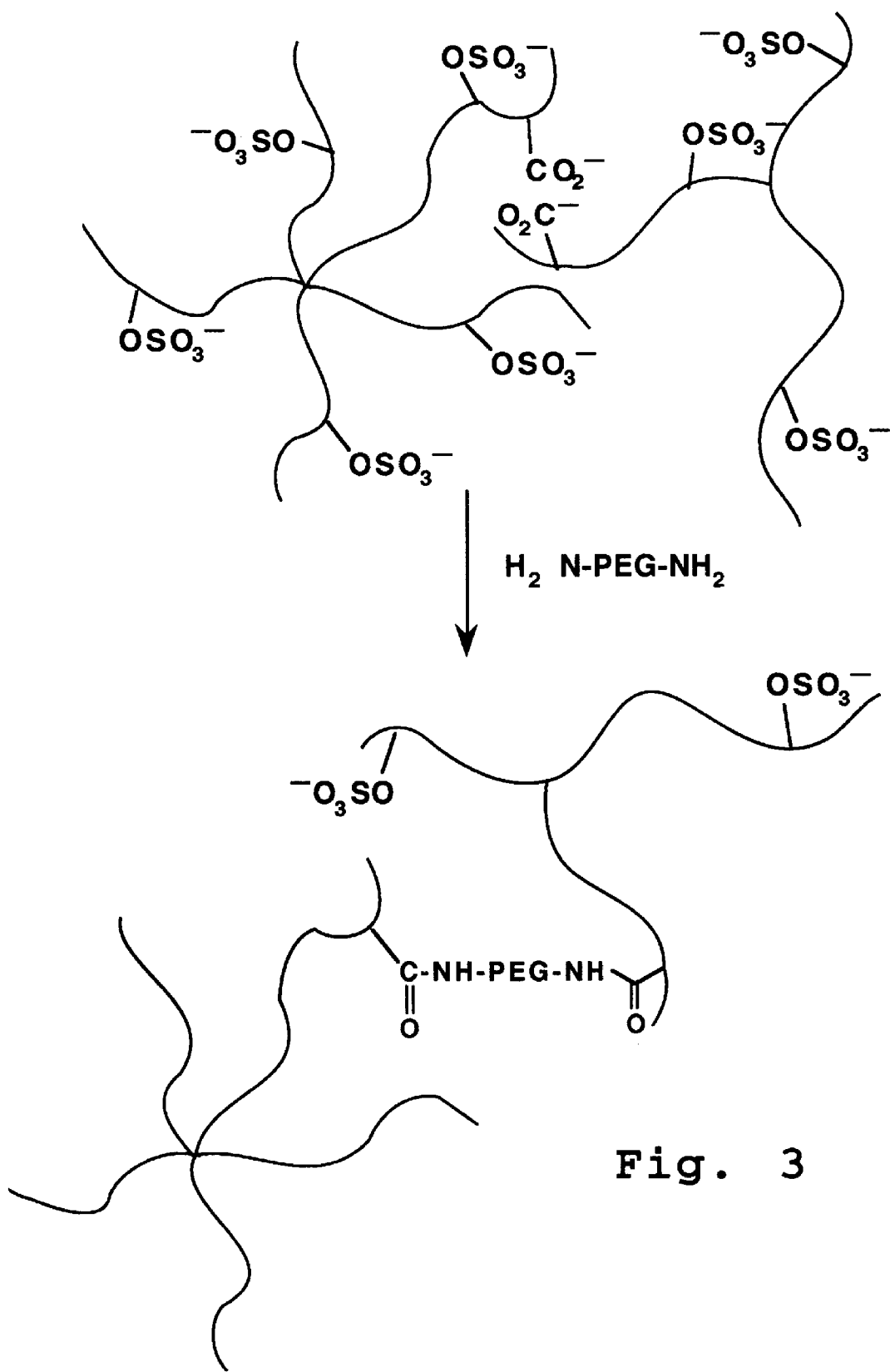
FIG. 3 shows a crosslinking reaction used in forming a crosslinked polymer matrix for use in the invention.

FIG. 3 illustrates one exemplary crosslinking reaction in which carboxyl groups in sulfated heparin side chains, such as shown at top in the figure, are linked by an activated diamino-PEG molecule, as indicated. Methods for activating crosslinking agents of this type, and for crosslinking polymer filaments by the activated agents, are well known (Wong, Antonietti, Huang, Funke). Alternatively, the carboxyl groups may be activated, for reaction with free amine groups in the crosslinking polymer.

The crosslinking reaction is preferably one which can be initiated by heat, e.g., by raising the temperature of the reaction by infrared irradiation, or by radiation, such as visible light, UV or X-irradiation, according to known polymer forming reactions.

2. Polymer synthesis

In another general embodiment, the charged polymer filaments are formed de novo in a polymerization and crosslinking reaction. A variety of monomer systems for forming crosslinked microparticles have been proposed, for example vinylpyridine, 2-hydroxyethyl methacrylate, acrylamide, dimethylacrylamide, acrolein, poly(N-isopropylacrylamide, amino acid monomers, saccharide monomers, alkylcyanoacrylates, glycidyl methacrylate, and hyaluronic acid (e.g., Wu, Arshady, Margel, Okubo, 1992a, 1992b, Kreuter, Kamei, Fujimoto, Yui, and Hosaka).

These monomers are mixed with selected charged-group monomers, such as methacrylic acid, vinyl monomers having carboxyl or amine groups (Arshady) or monomers in which the reactive group has been converted to a sulfate, sulfonate, or phosphate group, by standard reaction methods. Typically, the charged monomer will be included in a range from about 5–50 mole percent of uncharged monomer, although the polymer may be formed entirely from charged monomer units.

The polymerized chains may be crosslinked by free radical polymerization, by inclusion of crosslinking monomers, such as methylene-bis-acrylamide or divinylbenzene (e.g., Okubo, Arshady, Kreuter), or by crosslinking through polymer chains, as above.

In both of the approaches discussed above, the polymer filaments may be modified, before or after crosslinking to form microparticles, to introduce charged groups, and/or binding groups on the filaments. Thus, the initial microparticle may be formed of substantially uncharged filaments as long as the filaments contain groups that can be modified to form the desired charged group.

Similarly, the charged groups can be introduced by forming the microparticle to include a ligand-specific binding agent, such as lectin, and introducing the complement of the binding agent, e.g., sulfated heparin, into the matrix after particle formation (Tanaka).

The polymer filaments can be constructed and/or modified after particle formation to achieve desired characteristics. For example, when the polymer matrix is to be condensed or decondensed within a desired pH range, the polymer is prepared to include the charged group, e.g., carboxyl group or amine group, whose $pK_a$ is within such pH range.

Similarly, where the polymer matrix is to be used in delivering selected biological or chemical ligand species, preferably charged species, the microparticle is formed to include binding molecules capable of binding the ligand specifically and with high affinity.

D. Microparticle Formation

Several methods are available for forming microparticles having desired sizes in the size range 0.05 and 50 $\mu$m, preferably 0.05 to 0.5 $\mu$m. These include:

1. Emulsion Polymerization

In this method, monomers are dissolved in a continuous aqueous phase also containing emulsifier micelles plus excess free monomer stored in large droplets in suspension. Polymerization reactions, such as by addition of an initiator molecule or high-energy radiation, leads to polymerization in the regions of the micelles. Phase separation and formation of solid particles can occur before or after termination of the polymerization reaction. Particle size can be controlled by monomer density, micelle density, and polymerization conditions (Kreuter, Cadan, Vanderhoff). As with several of the published methods cited herein for microparticle preparation, it will be appreciated that the published method may need to be modified to include a desired percentage of charged monomers, as discussed above.

2. Emulsion Polymerization in Continuous Organic Phase

In this method, water-soluble monomers are added to a water-in-oil emulsion stabilized by a surfactant, under conditions that polymerization is initiated in the aqueous phase droplets (Kreuter).

3. Precipitation Polymerization

Precipitation polymerization involves polymerization starting from a monomer solution in which the polymer (or microparticle) is insoluble (Kawaguchi, 1991, 1992, 1993, Pelton, 1986, 1988, Tai). Typically in this method, polymerization of monomers in solution is allowed to proceed until desired size polymer filaments are formed, usually under conditions of vigorous mixing.

This method (following Kawaguchi) was followed in preparing synthetic microparticles described in several drug-loading and condensation studies reported below, where the crosslinked polymers described in the reference were prepared to include carboxylated subunits. The polymer mixture included methacrylic acid (10 mmol)/nitrophenyl acrylate (10 mmol)/methylene bis acrylamide (5 mmol)/ethanol (35 g), employing 0.75 g initiator AIBN. The reaction was carried out at 60° C. for 22 hours under nitrogen. The particle may be treated by reaction with ethylene diamine 100 eq/1 eq particle at room temperature for 48 hours.

4. Encapsulated polymer method

In this method, a polyanionic, hydrophilic polymer is crosslinked in an encapsulated form, followed by removal of the encapsulating membrane to leave cross-linked, decondensed particles of a desired final size. The method is illustrated in FIGS. 4A–4D for the preparation of particles using encapsulating lipid vesicle membranes.

Figure 4A:
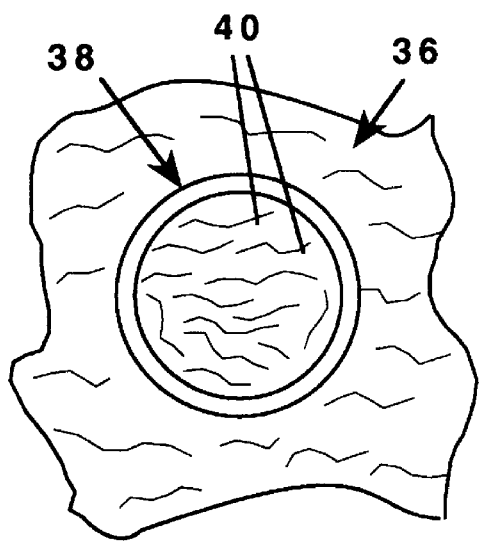
FIGS. 4A–4D illustrate steps in forming polymer-matrix microparticles by lipid encapsulation.
Figure 4B:
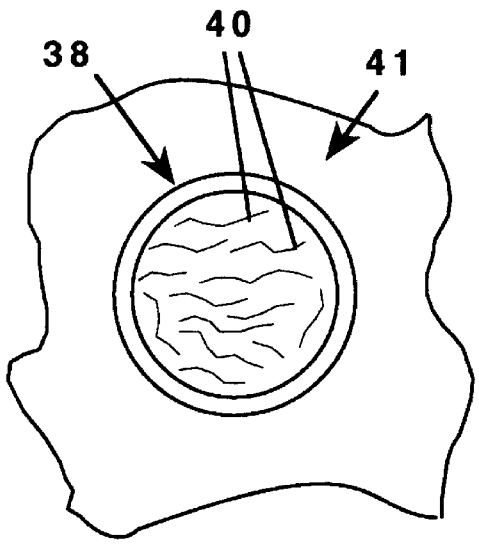

Initially, and with reference to FIG. 4A, an aqueous solution or suspension of the polymer and cross-linking agent (aqueous polymer medium) is encapsulated in lipid bilayer vesicles. A variety of vesicle-forming methods, such as lipid hydration, reverse-phase evaporation, solvent injection, and freeze-thaw methods are available for encapsulating aqueous material in lipid vesicles.

In a preferred method, the aqueous polymer medium is used to hydrate a dried lipid film formed of vesicle-forming lipids, such as a mixture of phosphatidylcholine (lecithin) and cholesterol. The hydration is carried out under mild agitation, to form liposomes with heterogeneous sizes between about 0.05 and 20 microns. The suspension, indicated at 36 FIG. 4A, contains liposomes, such as liposome 38 with encapsulated polymers, such as polymers 40, as well as polymers in the bulk phase of the suspension, as shown.

Figure 14A:
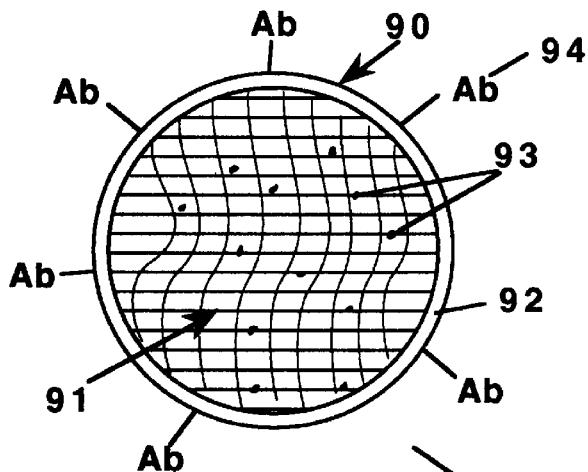
FIGS. 14A–14C illustrate the activation of an encapsulated microparticle like that shown in FIG. 13 (14A) by cell lysis in the presence of antigen and complement (14B), and the cascade of events leading to rapid released of entrapped compound in the microparticle's matrix (FIG. 14C)
Figure 14B:
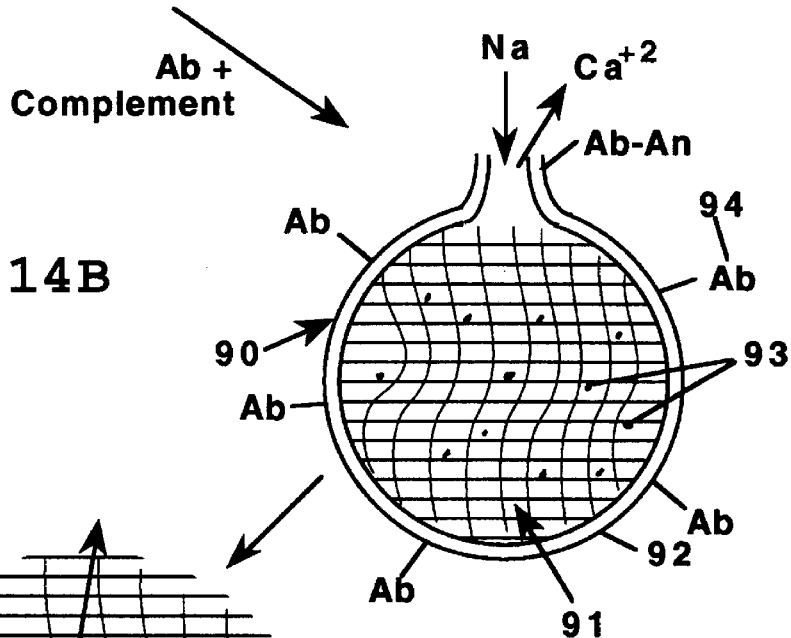

The liposome suspension may be sized, as by extrusion through a polycarbonate membrane or the like to reduce the largest liposomes to a desired upper size, e.g., 2–5 microns. Following this, the suspension may be further size fractionated, for example, by molecular sieve chromatography, to remove liposomes below a selected size range, e.g., 0.5 microns. At the same time, or in a separate step, the liposomes are separated from bulk-phase polymer material, to produce a suspension 41 of liposomes in a polymer-free aqueous medium, as shown in FIG. 14B.

Figure 4D:
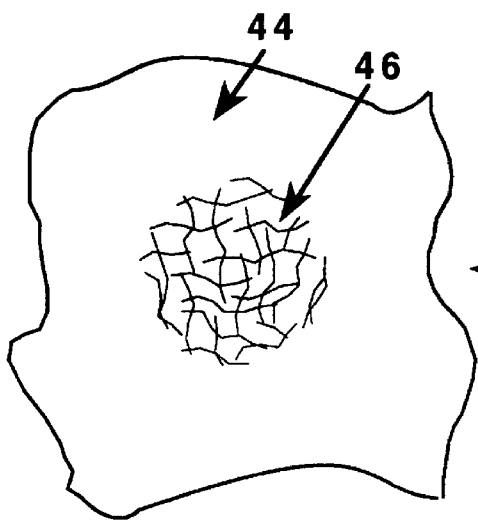
Figure 4C:
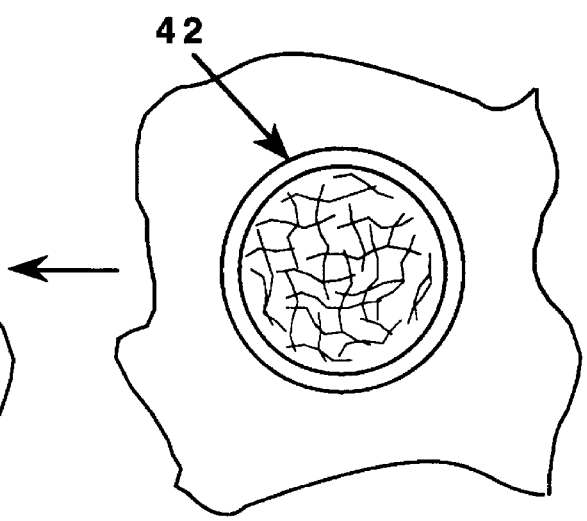

The liposome suspension is now subject to heat or irradiation treatment to initiate crosslinking of the encapsulated polymer suspension, as shown in FIG. 4C, according to standard methods such as outlined above. The cross-linked matrices, such as matrix 42, have the approximate sizes of the encapsulating liposomes.

In the final step, shown in FIG. 4D, the suspension is treated to remove the encapsulating liposome membranes, leaving a suspension 44 of the crosslinked particles, such as particle 46. Membrane dissolution may be produced by detergents, organic solvents, or the like. The microparticles may be separated from the lipid and lipid-solvent components by filtration or the like, then resuspended in an aqueous medium for further processing.

5. Gelatin Dispersion

This is a specific embodiment of a more general approach in which the polymer filaments or monomer subunits used in forming the microparticles are mixed with a suspension of proteins, such as agar, gelatin, or albumin (Kreuter, Tanaka). One method employs alginate plus $Ca^{+2}$ in producing the particles. The mixture is then dispersed under conditions effective to produce desired sized particles containing the mixture components. In the case of gelatin containing particles, the mixture may be cooled during the dispersion process to produce gelled particles having a desired size.

The particles are then treated under polymerization and/or crosslinking conditions, preferably under conditions that do not also lead to crosslinking of gelatin molecules to the polymer structure. After microparticle formation, the gelatin molecules may be removed from the structure, with such in a decondensed form, e.g., by heating the material or enzymatic digestion.

Other methods for forming microparticles have been reported, and are contemplated herein for use in preparing charged-polymer microparticles having the properties and characteristics discussed above.

Polymer-matrix microparticles having the rapid condensation/decondensation properties described above can also be made synthetically by a variety of methods. The microparticles are made by forming cross-linking polyionic hydrophilic polymers under conditions which lead to cross-linked matrices in the 0.05 to 50 µm, preferably 0.05 to 5 µm particle-size range, when the particles are in their condensed states.

III. Condensed-Phase Microparticles for Compound Storage

In one aspect, the invention includes a method of storing a compound, typically an unstable hydrophilic compound, but also including stable and/or hydrophobic compounds, as discussed below. The method includes infusing the compound into polymer microparticles of the type described above, with such in a decondensed phase, and after compound infusion into the open particle matrices, adding multivalent counterions to the medium under conditions effective to fully condense the microparticles.

When the microparticle formed in accordance with the above methods is suspended in a decondensing aqueous medium, typically one containing a 10–200 mM concentration of monovalent counterions, it is fully hydrated and has a size that is typically 3–4 times larger than the desired condensed-phase particles.

With addition of a multivalent counterion, such as $Ca^{+2}$ or histamine in the case of a polyanionic polymer matrix, the particle will be forced into a condensed phase.

In their condensed phase, the microparticles are substantially dehydrated, and have a water content that is less than about 30 percent, preferably less than about 5–15 percent by volume of water.

To determine the approximate water content of the microparticles in their condensed phase, the size of the particles can be compared before and after complete hydration, e.g., by suspending the particles in 100% ethanol. Particles which by this criterion typically contain less than about 30% by volume, preferably less than about 5–15% by volume of entrapped water, are suited for use in the method.

In practicing the method, particles prepared and selected as above are suspended in an aqueous decondensing medium in the presence of the hydrophilic compound to be stored. The compound is typically one which cannot be stored or is difficult to store either in solution or in a dehydrated form. The compound may be difficult to store either because it loses its activity, or forms undesired side products, or tends to aggregate or otherwise loses its solute properties when stored in an aqueous medium or when dehydrated, e.g., by lyophilization.

One general class of compounds suitable for use in the method are small, water soluble drug molecules, as exemplified by aminoglycoside antibiotics, such as doxorubicin or daunorubicin. The aminoglycoside compounds tend to promote, and in turn undergo, free radical reactions that lead to a loss of activity and/or appearance of more toxic side products. Other small drug compounds, particularly those capable of chelating iron or other metals, those capable of absorbing visible light, and those capable of acting as substrates for contaminating enzymes, such as esterase, may also show instability on storage in solution and/or in a dehydrated form.

A second general class of compounds suitable for use in the invention are polypeptides, including both peptides and proteins, such as peptide hormones, e.g., insulin, cytokines, and a large number of enzymes. Peptides or proteins may be unstable due to aggregation on storage or on drying, denaturation on freezing or drying, dissociation into inactive subunits, proteolysis in solution, free-radical or oxidative damage that occurs on storage, progressive inactivation in the absence of critical factors or co-factors, or intermolecular crosslinking or polymerization.

Still another general class of compounds suitable for the invention are the water soluble vitamins, such as flavin-containing vitamins and ascorbate.

Other general classes of water-soluble compounds that are difficult to store in solution or on dehydration, such as free-radical initiators, dyes, and unstable water-soluble organic compounds are also contemplated.

The compounds are preferably ionized or ionizable at a selected pH, and have a net charge in an ionized form which is opposite to that of the charged groups on the matrix filaments. In the case of a particle matrix formed of polyanionic filaments, the compounds have charged or ionizable amine groups that provide a positive charge to the compound at a selected pH, preferably between pH 6–10. Where the compound is a polypeptide, the number of positively charged amine groups should be in substantial excess of the number of negatively charged carboxyl groups.

Similarly, where the compound has a negative charge at a selective pH, such as ascorbate, or negatively charged polypeptides, the microparticle matrix is formed of polycationic filaments.

To prepare the condensed-phase microparticles, the compound to be stored is mixed in an aqueous medium with a suspension of microparticles in a decondensed phase. The concentration of compound in the suspension is typically between about 0.05 and 10 mM. The concentration of microparticles is preferably such as to allow substantially complete saturation of the matrix charge groups by the charged compound. This should occur at an effective compound concentration of up to 100–500 mM or greater for small drug molecules, and at a proportionately smaller concentration for multivalent species, such as polypeptides.

The ionic composition of the medium is such as to retain the microparticles in a decondensed condition, preferably including a low concentration of monovalent counterions, e.g., 10–200 $Na^+$. The pH of the medium is preferably between the $pK_a$ of the matrix polymer filament charge groups and the $pK_a$ of the compound charge group(s), insuring that both groups will be charged and capable of forming electrostatic bonds with one another.

The mixture is allowed to incubate, e.g., at room temperature, until the matrix has become fully saturated with the compound. The kinetics of compound uptake into the drug may be followed by a variety of standard methods, e.g., by removing aliquots of suspension at periodic intervals, condensing the particles, washing the particles to remove non-entrapped drug, and assaying the condensed particles for the presence of entrapped compound.

After a desired loading level is reached, preferably at or near saturation, the matrix is condensed by addition of multivalent cations, such as $Ca^{+2}$ and/or histamine. The final concentration of condensing counterion is preferably between 5–100 mM.

Figure 5:
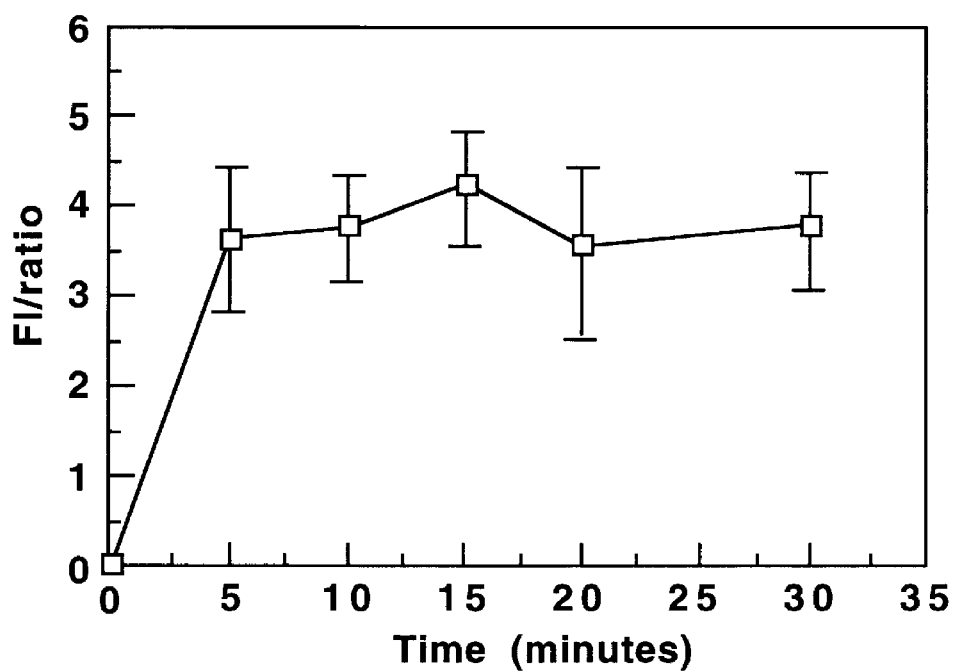
FIG. 5 shows a plot of doxorubicin loading into decondensed microparticles.

FIG. 5 shows a plot of uptake of doxorubicin into crosslinked heparin microparticles, such as isolated in accordance with Example 1. At an compound concentration of 0.5 mM, compound loading to a final effective concentration of about 200 mM was achieved after 30 minutes. At a compound concentration of 0.1 mM, loading to the same level was achieved after about 45 minutes. Similar results were obtained with synthetic microparticles.

As seen from the above, the charged drug compound partitions into the microparticles with a partition coefficient, with respect to the aqueous medium, of over 1,000. Thus, according to one advantage, the method of the invention provides a compound-concentrating effect for loading high levels of compound into the particles from a low aqueous loading concentration.

The effective concentration of compound in the loaded microparticles may be several times greater than the maximum solubility of compound in the aqueous loading medium. This is true particularly in the case of a compound with lipophilic character, since the condensed phase matrix will provide a low-hydration environment.

Figure 6A:
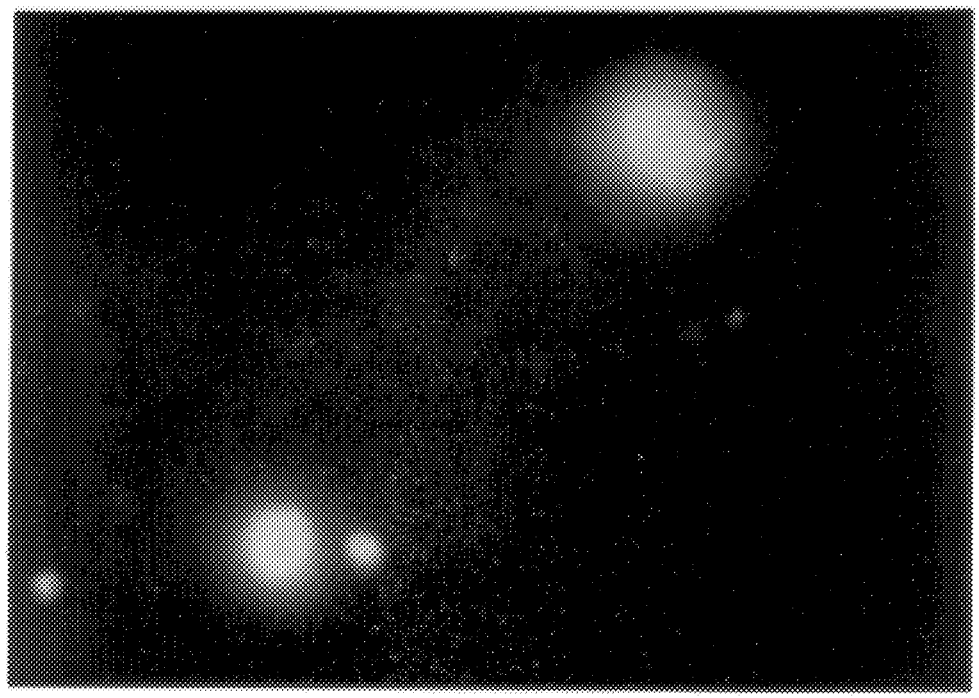
FIGS. 6A and 6B are photomicrographs of a condensed-phase mast-cell (6A) and synthetic (6B) microparticles loaded with doxorubicin.
Figure 6B:
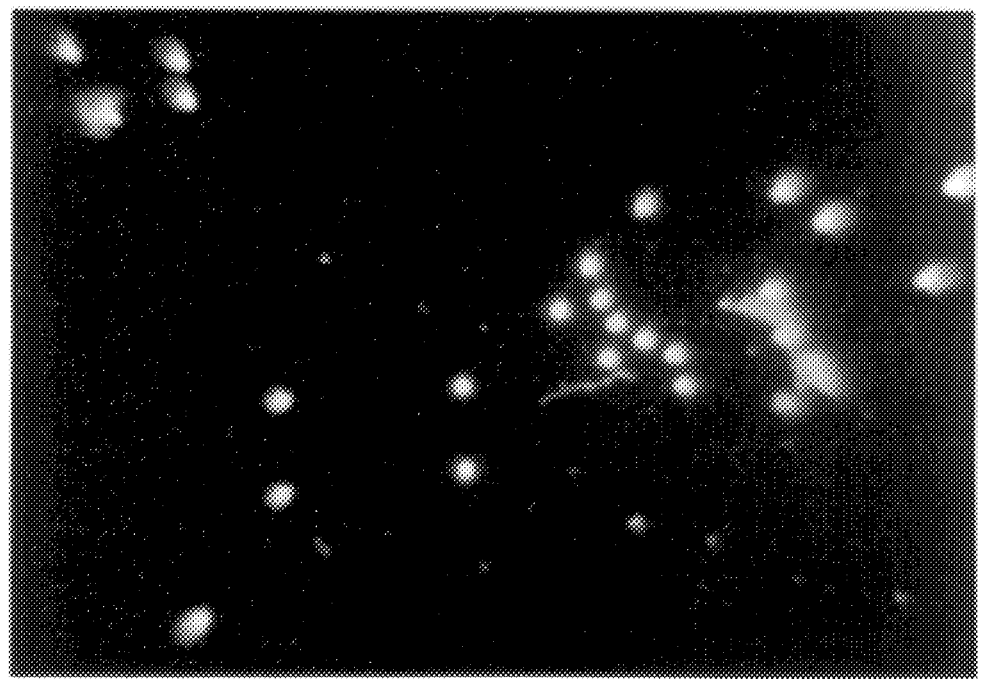

FIGS. 6A and 6B show heparin cross-linked microparticles from mast cells and synthetic microparticles, respectively, after loading with doxorubicin. The size of the condensed polymers is about 3 $\mu$m for the heparin matrix particle, and about 2 $\mu$m for the synthetic polymer.

Typically, the particles in the condensed state have volumes which are about $\frac{1}{5}$–$\frac{1}{3}$ those of the decondensed particles, and have a water content between about 5–30% by volume of the particle. As indicated above, the residual water volume of the condensed-phase particles can be estimated from the reduction in size or weight after dehydration, e.g., by ethanol extraction.

In another embodiment, the compound to be stored is itself a multivalent counterion capable of condensing the matrix. Histamine is example of a small drug compound of this type. Small cationic or anionic polypeptides are other examples of compounds that are desired to be stored, and which also serve as condensing agents. FIGS. 8A, 8C, 8E, and 8G show light photomicrographs and fluorescent photomicrographs (8B, 8D, 8F, and 8G) microparticles treated under various condensation and decondensation conditions. In 8A and 8B, microparticles (prepared as in Example 1) were suspended in an aqueous medium, pH 3.5, under conditions of decondensation. The particles were then loaded with fluorescent-labeled histamine, 150 mM in the aqueous medium, causing condensation of the particles (8C). The fluorescent label in the condensed-phase particles observed on condensation was retained in a probe-free solution (8D) indicating that the entrapped histamine was not freely diffusible.

When the condensed-phase microparticles from above were suspended in a $Na^+$-containing medium, the particles quickly decondensed (8E) and the entrapped fluorescent label quickly diffused away (8F). A new cycle of condensation, this time by unlabeled histamine caused particle condensation (8G), but failed to increase fluorescence in the condensed-phase particles (8H), confirming that labeled histamine was indeed released from the particles after decondensation.

After particle condensation, the particles may be further processed to achieve desired solubility properties and storage conditions. Since the condensed-phase particles have excluded much of the water of hydration, the condensed particles may be treated at this stage to increase their surface hydrophilicity. For example, the particle surfaces can be chemically derivatized with hydrophilic moieties, such as short hydrophilic polymer chains, according to known chemical derivatization methods. More simply, the condensed-phase particles can be incubated with a surfactant, such as a bile salt or fatty-acyl-PEG or cholesterol-PEG surfactant, under conditions effective to cause partitioning of the surfactant into the outer surface of the microparticle, with the hydrophilic moiety of the surfactant being exposed to aqueous medium. Surfactants of this type, having PEG chains in the 1,000–5,000 dalton range are commercially available. The PEG coating may serve the additional function, in a parenteral therapeutic composition, of extending the blood circulation time of the PEG-coated, condensed-phase particles.

Alternatively, a coat of hydrophilic material, such as polylysine or other polypeptide can be formed on the condensed particles. One method for forming a protein polyvalent peptide coat on a condensed microparticle is described in Section IV.

Finally, in preparing the particle for storage, the composition may be washed for storage in an aqueous condensing medium, filtered or centrifuged to remove aqueous suspension medium, for storage in a condensed, partially hydrated form, or dehydrated, e.g., by lyophilization, for storage in a dried form. In another embodiment, the condensed-phase particles may be stored in an aqueous medium, preferably after washing the particles to remove the aqueous loading medium.

According to another important aspect of the invention, it has been discovered that the particles remain in a highly condensed form in aqueous suspension, showing little or no compound leakage from the condensed-phase particles, even after an extended storage period.

Figure 7A:
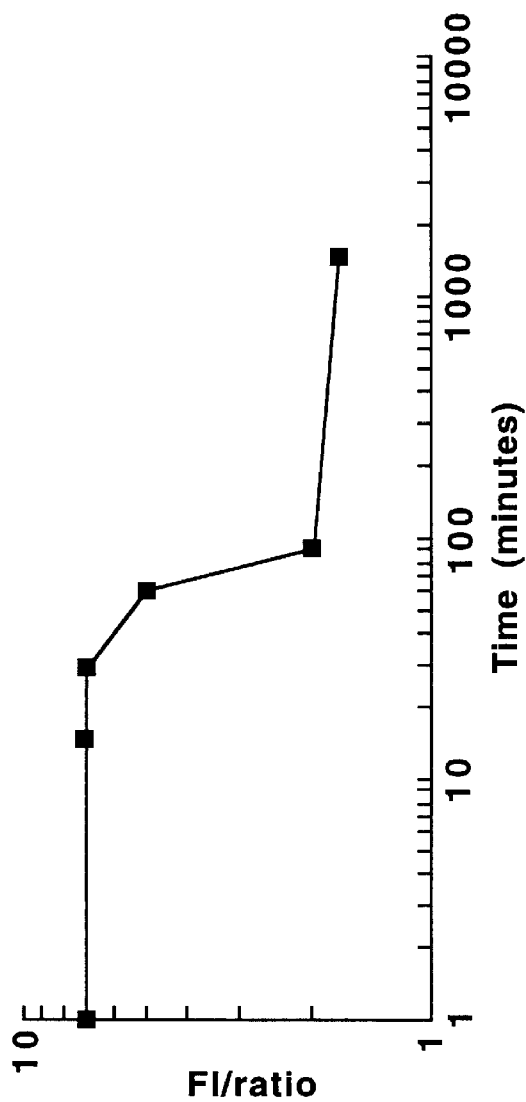
FIGS. 7A and 7B show the rate of release of doxorubicin from condensed-phase microparticles when stored in distilled water (7A), and when exposed to physiological saline (FIG. 7B)

FIG. 7A shows a plot of doxorubicin release rate from condensed-phase microparticles stored in distilled water. As seen, the half-life of drug release from the particles is about 1 hour, even though the distilled water medium is itself incapable of causing condensation of decondensed particles. The study illustrates the limited degree of diffusion of counterion and drug from the condensed-phase particles. When the particles are stored in partially dried form, or in an aqueous medium with condensing counterions, the particles may be stored without appreciable leakage over several weeks to months.

Figure 7B:
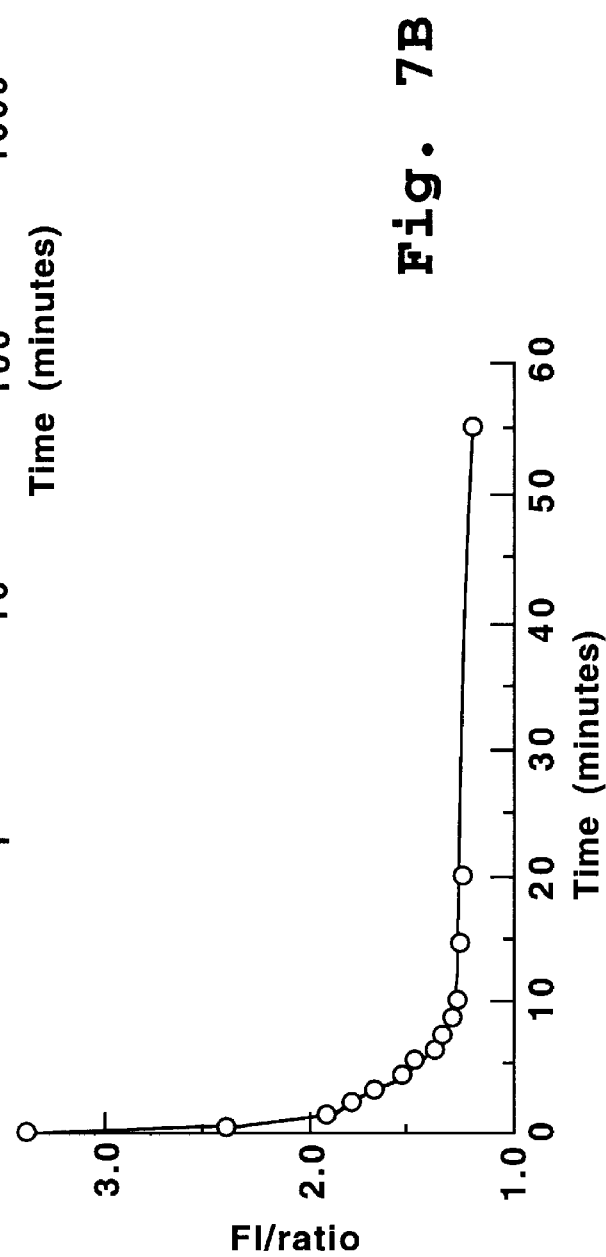

When the condensed-phase are suspended in 150 mM $Na^+$, i.e., decondensing conditions, the drug is rapidly released from the particles (FIG. 7B).

A composition containing the condensed-phase particles with entrapped compound is useful in therapeutic applications, as drug-delivery particles for parenteral, oral, or topical drug delivery. In parenteral use, the condensed-phase particles have the advantage first that a high concentration of water-soluble drug can be administered without severe osmotic effects at the site of administration, since the condensed-phase particles are essentially nonosmotic until they decondense and release drug.

Secondly, the compound can be stored, either in dry-particle or suspension form, with little loss of activity over an extended storage period. This feature is advantageous particularly for a variety of polypeptide which may otherwise be unstable on long-term storage.

Figure 9:
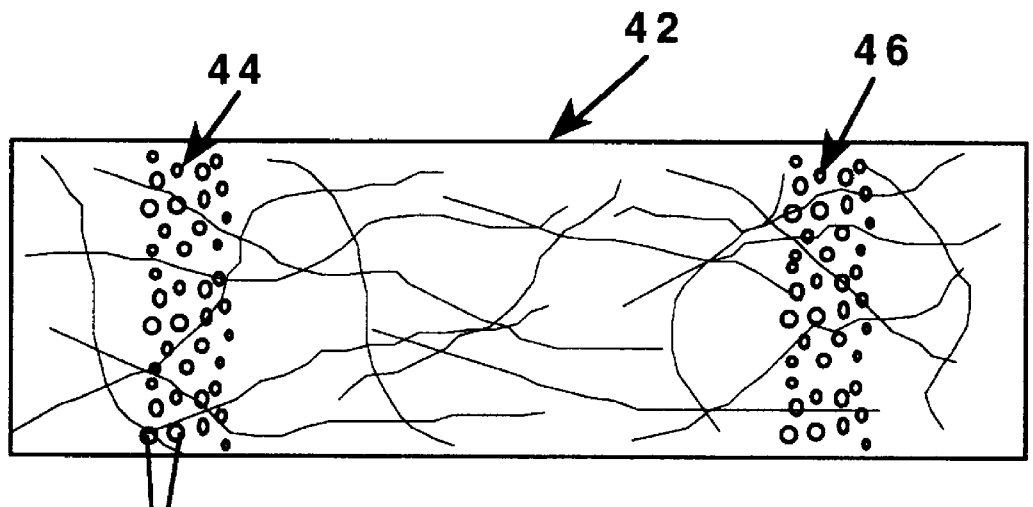
FIG. 9 shows a diagnostic device employing a condensed phase microparticle prepared in accordance with the invention.

The particles are also useful in diagnostic applications, both as a stable storage form of a diagnostic reagent, and as a means for providing rapid release of reagents under selected reaction conditions. FIG. 9 shows a dry diagnostic test strip 42 composed of a fiber mesh, and containing first and second compositions 44, 46 of dried (partially hydrated) condensed-phase particles, such as particles 48 in composition 44, constructed in accordance with the invention. The particles are immobilized in the mesh fibers as indicated.

The first composition contains a first assay reagent which is released into the strip on contact with a fluid sample, which contains a high concentration of monovalent ions. The first reagent may be, for example, an antibody capable of reacting with the analyte of interest, or an enzyme capable of acting on the analyte to produce an analyte-specific reaction product.

After reaction of the sample fluid with the first reagent, migration of the sample along the strip leads to release of a second reagent, producing a second reaction that is diagnostic for the presence of the analyte or analyte-derived molecules. The second reagent may be, for example, a dye or other reporter reagent.

One advantage of the condensed-phase particle composition in this application is the stable storage of reagent compound, such as enzymes, antibodies, and dyes in a diagnostics kit. Another advantage is the rapid release of entrapped compound on contact with aqueous medium or by other activating means, such as introduction of monovalent counterions. This is in contrast to the relatively slow release of particles in crystallized or aggregated form.

The composition is also useful as a delivery vehicle for reagents in chemical or biochemical reactions, where the reagent is unstable on storage, or where it is desirable to introduce the reagent at a selected step in a reaction, e.g., by decondensing the particles with a monovalent counterion.

IV. Delayed Release Particle Composition

In another aspect, the invention includes a compound-release composition formed of a suspension of microparticles having average sizes in a selected size range between 0.05 and 50 $\mu$m, preferably 0.5 to 5.0 $\mu$m. For use in parenteral drug deliver, the microparticles preferably have sizes between 0.05 to 0.5 $\mu$m.

Each microparticle is composed of a condensed-phase matrix of crosslinked polyionic polymer filaments capable of expanding to a decondensed phase in the presence of monovalent counterions. The matrix contains entrapped small molecules, such as therapeutic or reagent molecules, and polyvalent counterions, preferably polyvalent polymer molecules, effective to delay the release of the small molecules from the microparticles, when the microparticles are exposed to monovalent counterions.

In a related aspect, the invention includes a method of delaying the release of small molecules entrapped in a condensed-phase polyionic microparticles of the type described above, by condensing the microparticles, either partially or completely, with polyvalent counterions selected to produce a desired rate of particle decondensation in the presence of monovalent counterion.

In one general embodiment, described in Section A, the polyvalent counterion is relatively small and capable of readily diffusing throughout the matrix, acting as the sole condensing agent. In a second general embodiment, described in Section B, the polyvalent counterion is poorly diffused into matrix, by virtue of its size or solubility properties, and is taken up in an outer shell region of the matrix only, with complete particle condensation occurring by a small multivalent counterion, such as $Ca^{+2}$.

A. Delayed Release Microparticles

Figures 10A, 10B:
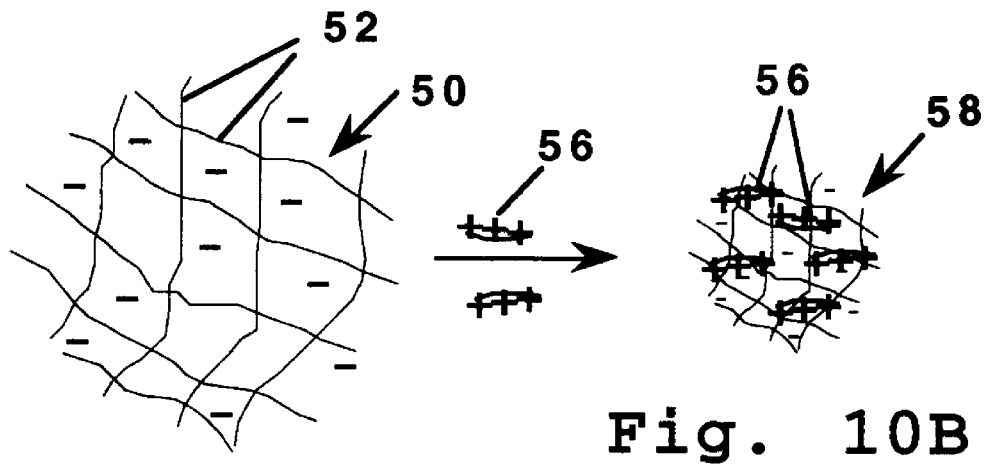
FIGS. 10A and 10B illustrate steps in preparing a condensed phase microparticle in a compound-release composition constructed in accordance with another embodiment of the invention.
Figure 11A:
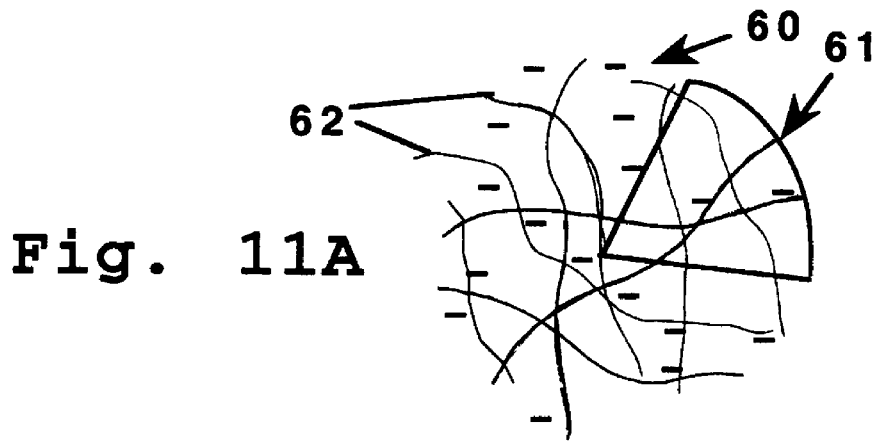
FIGS. 11A–11C illustrate steps in preparing a condensed phase microparticle in a compound-release composition constructed in accordance with one embodiment of the invention.
Figure 11B:
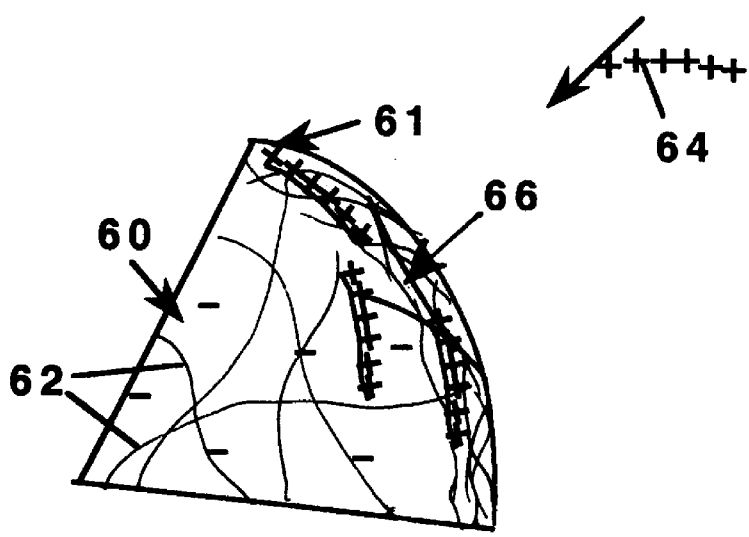
Figure 11C:
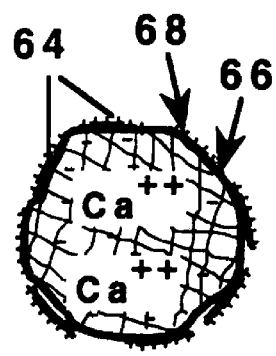

FIG. 10A illustrates a decondensed polyionic matrix 50 of the type described above, which in this embodiment, is formed of crosslinked polyanionic filaments, such as filaments, 52. The matrix is preferably infused with a small compound (not shown) which is to be delivered from the particle. Compounds which are suitable for entrapment in condensed-phase microparticles are discussed above.

The particles with infused compound are condensed with a polyvalent counterion capable of diffusing through the matrix, with such in its decondensed form. In FIGS. 10A and 10B, the condensing agent is a trivalent counterion indicated at 56. The condensing agent produces a condensed-phase particle, such as indicated at 58, with the condensing agent and entrapped small molecule distributed throughout the matrix, as indicated. An example of such a condensing agent is the peptide mastoparan, a 14-amino acid peptide having three positively charged groups. Other polycationic polymers, including other polypeptides with multiple lysine groups, or polyamine polymers, including polyquaternary amines, are also suitable. The sizes of the polyvalent species is preferably less than about 5–10 Kdaltons, and preferably has no more than about 5–10 charged groups/molecule.

The concentration of polyvalent condensing agent needed to produce full particle condensation may be substantially lower, with respect to the concentration of monovalent counterions, than is required for particle condensation with a divalent counterion, such as $Ca^{+2}$ or histamine. For example, 1 mM mastoparan is effective to produce complete condensation of particles in the presence of 150 mM Na salt. In general, the higher the valency, the more strongly the condensing agent can be expected to displace monovalent counterions in the matrix, and the lower the ratio of polyvalent/monovalent counterions that will be required for achieving particle condensation.

The particles are incubated with the condensing agent until complete particle condensation has occurred. As above, the degree of condensation may be monitored by observing changes in size and or amount of residual water present. The time required for condensation may be on the order of several minutes or more, and will generally depend on the size of the polyvalent species, and the size of the condensed-phase microparticles.

After complete condensation, the particles may be further processed, as above, by washing and/or storage in a dried state.

According to an important feature, the polyvalent species used to condense the particles can be selected to control the rate of particle decondensation when the condensed-phase particles are exposed to monovalent counterions. As indicated above, polyvalent counterions having high valency, e.g., 5–10 charged groups per molecule, give slower decondensation times than lower-valency counterions, e.g., 3–5 charged groups. Microparticles (2–3 μm) condensed with mastoparan (a trivalent species) showed decondensation times of about 15–20 minutes when exposed to medium containing about 150 mM $Na^+$. This contrasts with the rapid decondensation (e.g., 2–30 secs) that occurs in 2–3 μm size condensed-phase microparticles condensed with divalent counterions.

For therapeutic applications, the composition is prepared to achieve a desired rate of decondensation and drug release in a physiological medium, such as the upper gastrointestinal tract or bloodstream. This may be done by increasing the valency of the counterion until a desired swelling rate in vitro is observed in a selected swelling medium. As in the mastoparan example, the condensing agent itself, e.g., a charged polypeptide, may be the therapeutic molecule itself.

B. Charge-Coated Microparticles

In another embodiment, illustrated in FIGS. 11A–11C, the microparticles are condensed under conditions effective to include the polyvalent species in an outer surface region only of the condensed microparticles.

FIG. 11A illustrates a decondensed polyionic matrix 60 of the type described above, which, in this embodiment is, formed of crosslinked polyanionic filaments, such as filaments, 62. The matrix is preferably infused with a small compound (not shown) which is to be delivered from the particle. Compounds which are suitable for entrapment in condensed-phase microparticles are discussed above. The sector 61 in FIG. 11A is shown in enlarged view in FIG. 11B.

In this embodiment, particle condensation involves two condensing agents. The first agent, illustrated in FIG. 11B, is a relatively large polyvalent species, such as polypeptides or other charged polymers, and indicated here at 64. This agent is effective to penetrate into the outer region of the matrix only.

The effect of the first condensing agent is to partially condense an outer surface region 66 of the matrix which now contains bound polyvalent molecules. The second condensing agent is one capable of readily diffusing into condensing the entire matrix. This agent may be a divalent or polyvalent counterion species of the type discussed above. The second condensing agent is effective to form condensed microparticles, such as microparticle 68 in FIG. 11C, having a surface coating 66 of the polyvalent molecules 64, and small molecules (not shown), such as therapeutic molecules, entrapped in the matrix.

In the embodiment just described, the condensed-phase particle was formed by addition first of the large polyvalent species, and subsequent condensation with a small counterion. The two condensation steps may be carried out together, or in reverse order. To illustrate the latter approach, the particles may be first condensed with a small polyvalent counterion which leads to slow decondensation, then partially decondensed by a monovalent counterion, and finally fully recondensed by addition of the large polyvalent species. The latter approach has the advantage of forming a more dense packing of polyvalent species in the outer surface region of the microparticles, for achieving slow rates of decondensation.

As above, the polyvalent agent used to condense the outer surface region of the polymer may itself be a therapeutic molecule, such as a charged polypeptide.

The method just described may also be employed in forming condensed-state microparticles having a desired surface coating. This method is illustrated in FIGS. 12A and 12B. Here it is desired to coat the microparticles with polyethyleneglycol (PEG) polymer strands to achieve enhanced circulation time of the microparticles in the bloodstream. In the method, a decondensed matrix, such as shown at 70 in FIG. 12A is incubated with a large polyvalent molecule 72, such as a positively charged polypeptide, that has been derivatized with PEG chains, such as indicated at 74. Addition of a small condensing agent, such as $Ca^{+2}$, either before, during, or following the surface coating step, as discussed above, produces a condensed-phase microparticle 78 having a surface coating 76 of the desired polymer.

V. Encapsulated Microparticle Composition

This section describes a particle composition for rapid release of an entrapped compound at a target site, and methods for producing the composition. The suspension is designed to release a particle-entrapped compound when the particles of the composition are exposed to a selected target condition related to pH, temperature, or the presence or absence of a selected ligand, such as an antigen or an antibody. According to an important feature of the invention, the target condition is effective to trigger rapid release of the compound, by an amplified or cascade ion influx mechanism.

The composition is formed of a suspension of encapsulated microparticles, such as microparticle particle 80 shown in FIG. 13. Each particle includes a polymer-matrix microparticle 82 of the type described above, with such in a condensed phase, and a lipid bilayer membrane 84 encapsulating the microparticle. The compound to be released, such as indicated at 86, is entrapped in the condensed particle matrix. The encapsulated contents of the particle also includes a multivalent counterion at a concentration sufficient to maintain the microparticle in a condensed state. The lipid membrane has a surface coating of anti-ligand molecules, such as molecules 88, as described below.

A. Preparing Encapsulated Microparticles

To prepare the particle composition, polyionic-fiber microparticles of the type described above are prepared or isolated. The sizes of the microparticles, in a condensed state, are preferably in the size range 0.05 to $5\mu$ for preparation of a diagnostic composition and 0.05 to 0.2 $\mu$m for a drug-delivery composition. In preparing particles in a decondensed state, the sizes of the particles may be 2–3 times the desired condensed-state size.

Methods of entrapping a selected compound, preferably a water-soluble compound, follow the same methods discussed above in Section III and IV. For use in a drug-delivery composition, the compound may be any therapeutic compound suitable for entrapment in the condensed-phase matrix. Exemplary compounds include anti-tumor compounds, anti-bacterial, anti-viral, or anti-fungal agents, immunosuppressant compounds, and polypeptides, such as enzymes, cytokines, or peptide hormones including water-soluble, amphipathic, or lipophilic drugs. Preferred compounds are those which are ionizable or charged, and carry a charge opposite to that of the matrix polymer filaments, allowing high partitioning of the compound into the matrix,, as discussed above. According to one advantage of the invention, the drug in this mixture may be present in a partially insoluble form, either because the drug is a lipophilic compound having low aqueous solubility, or because the drug, though hydrophilic, is present at a concentration above its normal water solubility.

For preparing particles for use as a diagnostic reagent composition, the compound may be a detectable reporter, such as a colored or fluorescent reporter, or an enzyme, or may include one or more assay reagents, such as ligands, antibodies, enzymes, and/or enzyme substrates.

After mixing the compound(s) to be released and the decondensed particles under conditions effective to infuse the particle matrices with the compound, the particles are transformed to a condensed state by addition of multivalent counterion species, to a concentration sufficient to produce decondensing of the particle matrices. If necessary, e.g., where the concentration of monovalent counterions is relatively high, the particles may be condensed by exchanging divalent for monovalent cations in the mixture, e.g., by molecular sieve chromatography or dialysis. The condensing step serves to trap the matrix-infused drug in the particles.

The suspension of condensed particles is then treated, for example, by washing and centrifugation, to remove non-entrapped compound, and the washed particles are resuspended in aqueous medium containing multivalent counterions for maintaining the particles in their condensed state.

A variety of methods are available for encapsulating the condensed particles in lipid vesicle form (Szoka, 1980). Prior to forming the lipid coat, the condensed-phase particles may be treated, as described in Section III, to produce a hydrophilic coating on the particles.

In one lipid-coating method, liposomes containing a desired lipid composition are sonicated extensively to form small unilamellar vesicles (SUVs), preferably in the 30–70 nm size range, and the SUVs are lyophilized. A concentrated suspension of condensed particles, prepared as above, is added to this lyophilizate, preferably in an amount estimated to provide an encapsulated vesicle volume equal to the total microparticle volume.

After allowing the vesicles to rehydrate in the presence of the particle suspension, the vesicle/particle suspension is subjected to several freeze-thaw cycles, leading to larger uni- and oligolamellar vesicles encapsulating the microparticles. Nonencapsulated particles can be separated, for example, by centrifugation, from encapsulated microparticles. The encapsulated microparticles may be further processed to remove larger-size vesicles, e.g., those larger than $0.2–0.4\mu$, or to reduce vesicle size by standard membrane extrusion methods (Szoka, 1978).

Another method for encapsulating particles involves a reverse phase evaporation method of liposome formation (Szoka, 1980). To modify the method to the needs of the present invention, a concentrated aqueous microparticle suspension containing entrapped compound is emulsified in a solution of phospholipids in a lipophilic solvent, such as chloroform. The emulsion that forms is a water-in-oil emulsion made up of individual microparticles, each coated by a phospholipid monolayer. The emulsion is reduced to an unstable lipid gel by solvent removal.

With mechanical agitation, either with or without the addition of additional aqueous medium, the gel collapses to form oligolamellar vesicles with encapsulated microparticles. Further treatment may involve liposome sizing, as by extrusion through a defined-pore size polycarbonate membrane, and removal of nonencapsulated particles.

In a third general method, the condensed microparticles are suspended with membrane-forming lipids in an aqueous solvent containing a bile salt, alcohol, or other solvent components capable of destabilizing vesicle membranes. The mixture of lipids and particles is then treated, e.g., by dialysis, effective to remove the destabilizing solvent component, until stable lipid bilayer membranes form about the condensed particles.

The suspension of encapsulated particles may be further treated, e.g., by centrifugation or molecular sieve chromatography, to remove undesired solvent components or contaminants.

In a related method, the condensed microparticles are mixed with a suspension of lipid vesicles, under conditions that promote lipid exchange between the vesicles and particles. Typically, the mixing is carried out above the phase-transition temperature of the lipids. The reaction is continued until lipid bilayers have formed about the particles.

As above, the vesicles may be further processed to obtain desired sizes less than about $0.5\mu$, and to remove non-encapsulated microparticles.

C. Vesicle Membrane Properties

The encapsulated microparticles constructed in accordance with the invention are designed to allow localized vesicle lysis and counterion exchange across the vesicle membrane under selected target conditions.

In the embodiment of the invention illustrated in FIG. 13, the microparticles have surface-attached anti-ligand molecules, such as antibodies 88, that are part of a ligand-anti-ligand pair, where the antibody in the pair may include a ligand-specific antibody fragment, such as an $F_{ab}$ fragment.

Methods for coupling anti-ligand molecules to lipid bilayer surface groups are well known. Typically, the bilayer membranes are formulated to include lipids, such as phosphatidylcholine (PE), phosphatidylserine (PS), or phosphatidylinositol (PI) with reactive polar-head groups, such as amine, hydroxyl, or sugar groups, respectively. In one general approach, the anti-ligand molecules are activated, such as by reaction with N-hydroxysuccinamide (NHS) or other activating agent, then reacted with the particles, to covalently link the anti-ligand molecules to the outer-surface lipid groups.

In another general embodiment, the anti-ligand molecules are joined to the lipid membrane by reacting the particles with the anti-ligand in the presence of a condensing agent, such as dicyclocarbodiimide, or a suitable bifunctional reagent.

Alternatively, the anti-ligand may be initially conjugated to a lipid component, such as a phospholipid, and this lipid then used in preparing lipid-encapsulated particles. The anti-ligand in this embodiment is contained on both sides of the lipid bilayers in the encapsulated particles.

In another general embodiment, the liposomes are composed of lipids whose phase transition temperature is slightly above a selected temperature. For example, when designed for use in a drug-delivery composition, the lipids may be selected for stability at normal body temperature, but show increased leakiness at an above-normal temperature, such that the particles are relatively stable when administered in vivo, but are destabilized by hyperthermic treatment, as described below.

In another general embodiment, the liposomes contain lipids, such as lysolecithin, which can be readily degraded by phospholipase enzymes at a selected pH.

D. Amplified Compound Release

Figure 14C:
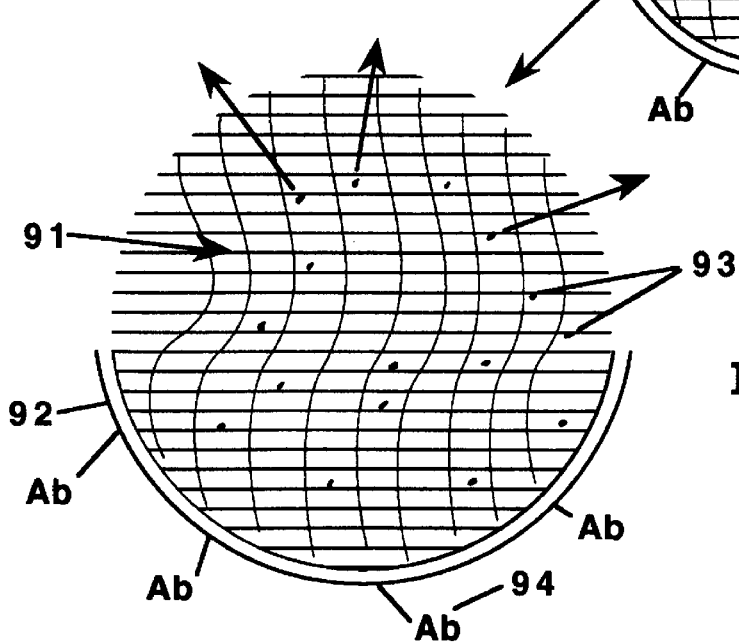

The encapsulating lipid membrane is designed to respond to the selected target condition, by allowing an influx of monovalent counterions, such as $Na^+$ present in the environment, and an efflux of internal multivalent counterions, through localized areas of membrane lysis. FIGS. 14A–14C illustrate the mechanism of amplified, cascade-type compound release from the particle composition of the invention. FIG. 14A shows an encapsulated microparticle 90 similar to the one shown in FIG. 13, having a condensed-phase microparticle 91 encapsulated in a lipid bilayer membrane 92. Entrapped compound in the condensed matrix is indicated at 93. The membrane has surface-attached anti-ligand antibody or $F_{ab}$ antibody fragments molecules 94 effective to bind to target-site ligand molecules.

The target condition that stimulates compound release from the particles is binding of the target-site anti-ligand molecules, such as an antigen (An), to the surface-bound antibodies. Where the composition is used for in vivo delivery of a therapeutic compound, the triggering binding event for compound release may occur at a bloodstream target site, or at a tissue site, e.g., at a site involving cell- or tissue-specific surface antigens.

Where the composition is designed to be used as a homogeneous-assay diagnostic reagent, as described below, the target site is a sample mixture containing a ligand analyte in solution.

Binding of the antigen to the surface-bound anti-ligand molecules, in the presence of blood complement components, leads to localized membrane lysis or rupture, as indicated in FIG. 14B. The areas of localized lysis allow influx of monovalent counterions, such as $Na^+$ and $K^+$, and efflux of encapsulated multivalent counterions, such as $Ca^{+2}$ or histamine. The monovalent counterions are present in a physiological environment, in a drug-delivery setting, or are included in the reaction medium, in an analyte assay.

This exchange of counterions across the membrane, at the point of localized lysis, produces a rapid localized decondensing of the encapsulated particle matrix, further rupturing the vesicle membrane and leading to increased counterion exchange.

The initial localized lysis thus sets off a cascade of events which lead to rapid swelling i.e., decondensing of the entire microparticle matrix, as illustrated in FIG. 14C. This mechanism is an amplified or cascade type mechanism, in that a small localized signal at the vesicle membrane is amplified by localized matrix swelling until the entire matrix has decondensed. The rapid decondensing acts to expel a portion of the entrapped compound and allows remaining drug molecules to diffuse into the surrounding medium, as shown in FIG. 14C. The series of events from localized lysis to complete swelling of the encapsulated matrix, preferably occurs in a period between about 1–10 sec or less.

Figure 15A:
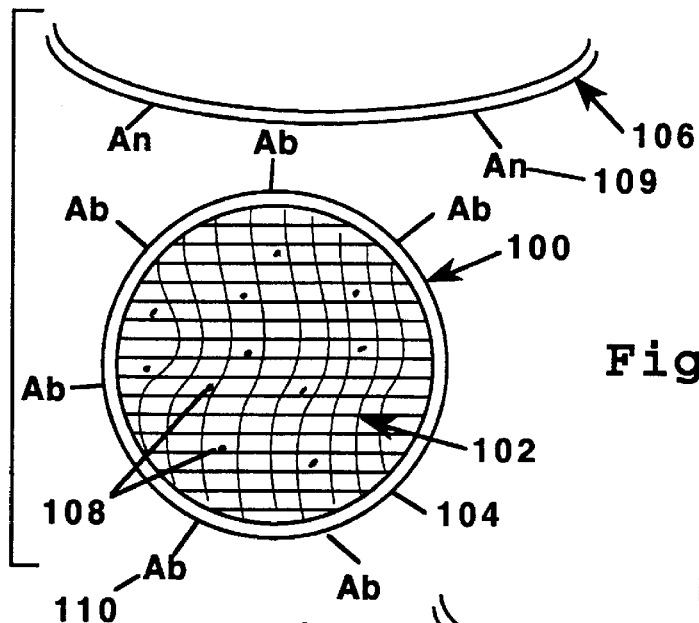
FIGS. 15A–15C illustrate attachment of an encapsulated microparticle (FIG. 15A) like that in FIG. 13 to the surface of a cell, with fusion of the microparticle and cell membrane (15B), and rapid decondensing of the microparticle's polymer matrix to release entrapped drug into the interior of the cell (15C).
Figure 15B:
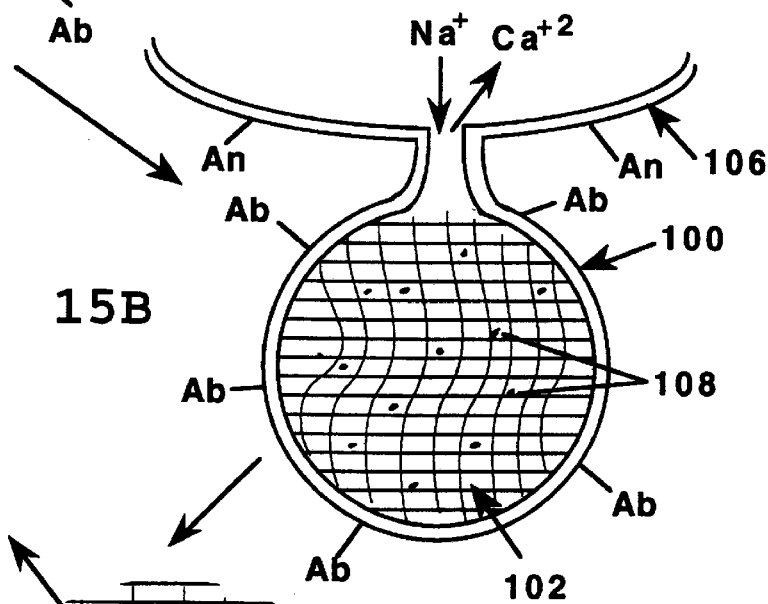
Figure 15C:
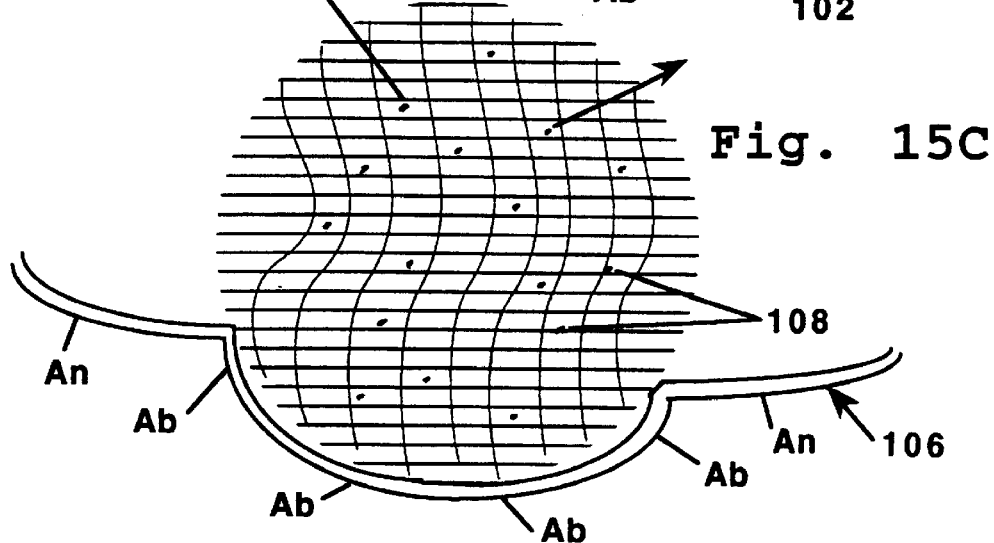

FIGS. 15A–15C illustrate rapid target-initiated compound release from a composition particle 100 at a target surface site, such as shown at 106. The encapsulated microparticle is composed of a condensed-phase matrix 102 having entrapped compound 108 and an encapsulating lipid bilayer membrane 104. The membrane contains surface bound anti-ligand molecules 110, such as antibody or antibody fragment molecules.

The target surface shown here is a cellular surface having surface-specific anti-ligand molecules 109, for use in targeting an in vivo cell surface site. As illustrated in FIG. 15B, this binding leads to localized fusion of the particle membrane with the cell membrane. The areas of localized lysis allow influx of monovalent cations, such as $Na^+$ and $K^+$, and efflux of encapsulated divalent cations, such as $Ca^{+2}$ or histamine, causing rapid decondensing of the encapsulated particle matrix, further rupturing the vesicle membrane and leading to increased cation exchange effects.

As above, initial localized lysis sets off a cascade of cation influx and matrix swelling that leads to rapid and complete expansion, i.e., decondensing of the microparticle, as illustrated in FIG. 15C, expelling entrapped drug into the target cell.

Where the composition is used as a diagnostic reagent in a solid-phase assay, the binding surface in FIG. 15A may be a solid-support surface having a surface-bound anti-ligand molecules capable of binding to the particle anti-ligand molecules, to bind the particles to the surface, in proportion to the amount of analyte also present in the reaction mixture. After washing the surface, to remove non-specifically bound material, the particles can then be lysed, e.g., by heating or hypoosmotic swelling, to release the compound, e.g., reporter molecule, contained in the particles.

D. Drug-Release Composition

In one general embodiment, the composition is designed as a drug delivery vehicle, for particle delivery to a selected in vivo site, with rapid release of the entrapped therapeutic agent at the site. The site is typically the bloodstream or a localized site accessible by the bloodstream.

For use in treatment, a suspension of microparticle vesicles of the type described above are administered, typically by parenteral administration, to reach a selected target site which can include circulating antibodies, specific organs or tissues, or a solid tumor site.

For parenteral administration, and in particular for intravenous administration in bolus form, the method allows higher drug doses to be administered because the drug may be present within the vesicles at concentration well above the drug's normal solubility, which may limit drug dosage in free form, or in conventional liposome-encapsulated form. Further, since the drug is not released until it reaches a target site, side effects due to generalized distribution of free drug are reduced.

Another important advantage of the method is the ability to achieve rapid, controlled drug release at a target site. Following vesicle administration, a portion of the vesicles localize at the target site in vivo, where the vesicles undergo partial lysis in response to selected conditions at the site, leading to a cascade of monovalent cation influx and divalent cation efflux, as described above, with rapid release of the entrapped drug at the site. This is in contrast, for example, to conventional lipid-vesicle drug delivery, where vesicle disintegration and drug leakage occur slowly over an extended vesicle-circulation time.

E. Diagnostic Particle Composition and Method

In a second general embodiment, the composition is designed for use as a diagnostic reagent, either for assaying an analyte by a homogeneous assay, or for use as a reagent containing a selected assay component.

A homogeneous assay employing the composition is illustrated in FIGS. 14A–14C, described above. Here a sample containing the analyte of interest (An in the figures) is mixed with the particle composition in the presence of blood complement. Binding of the analyte to the particle-surface molecules leads to complement-mediated lysis, initiating the cascade of events leading to rapid matrix decondensation and release of entrapped reporter compound.

The following example illustrates a method for isolating biological microparticles useful in the invention.

Example 1: Isolation of Mast Cells

Mast cell secretory granules were prepared from adult beige ($bg^j/bg^j$) mice (Jackson Laboratories, Bar Harbor, Me.) according to standard methods described by Monck et al., (1991), and modified to increase the number of intact isolated secretory granules. Cells were obtained by peritoneal lavage with a solution of the following composition (in mM): 136 NaCl, 1 $MgCl_2$, 2 $CaCl_2$, 22 $NaHCO_3$, 0.4 $K_2HPO_4$, 2 Glucose, 8.8 units/ml Heparin, 0.1% Bovine serum albumin (300 mOsm/kg, pH 7.3). Cells were resuspended in 1 ml, layered on 2 ml 22.5% wt/vol metrizamide and centrifuged at room temperature for 20 min. at 400 g. The pellet was resuspended in 1 ml of a $Ca^{2+}$, $Mg^{2+}$-free sonication buffer of the following composition (in mM): 130 NaCl, 10 KCl, 22 $NaHCO_3$, 0.3 $K_2HPO_4$, 0.1% Bovine serum albumin (300 Mosm/kg, pH 7.3). This suspension of purified mast cells was subjected to 4 sonication pulses at 25% of maximum power (sonicator model 45; Branson Sonic Power Co., Danbury, Conn.) and plated onto glass bottomed chambers and stored at 37° C. under 5% $CO_2$ atmosphere until use. An average of about 200 intact secretory granules per mouse were routinely obtained, that were osmotically stable with a half-life of over 3 h.

Isolated secretory granules were bathed in a standard solution containing (in mM): 25 NaCl, 125 Kcl, 2 $CaCl_2$, 1 $MgCl_2$, 0.2 ATP, 10 HEPES (300 Mosm/kg, pH 7.3).

Alternatively, mast cells were collected in a solution containing 150 mM NaCl, 10 mM Hepes, 3 mM KOH, 0.943 mM NaOH, 1 mM $MgCl_2$, 2 mM $CaCl_2$, and 12 mM glucose, 310 mmol/kg, pH 7.3, at room temperature. Secretion was stimulated by 10 ug/ml of compound 48/80 (Sigma Chemical Co., St. Louis, Mo.). Swelling of secretory granules was recorded using a Toshiba video camera (model IKC30M) mounted on an IM35 microscope (Zeiss) equipped with Nomarski optics including a 63× oil immersion Zeiss objective. (3500×, final magnification). The diameter of the granules was measured by single frame video image analysis at a sample rate of 30 frames/sec. Single frame images were played back from a VCR (BV-1000 Mitsubishi) and sampled by a frame grabber (DT 2851, Data Translation) operated by the Image-Pro software package (Media Cybernetics). Volumetric expansion was calculated assuming a spherical shape for the secretory granules. Size is conveniently expressed as a percent of final decondensed volume after exocytosis in external solution (pH 7.3). Granules were re-condensed to within 5% of pre-secretion volume by bathing in a solution containing 50 mM histamine, pH 3, devoid of other ions.

While the invention has been described with respect to particular compositions and method, it will be appreciated that various changes and modifications may be made without departing from the invention.

It is claimed:

1. A method of storing a positively charged therapeutic compound, comprising adding said therapeutic compound in a medium to polymer microparticles having selected sizes in the 0.02 to 5.0 micron size range, where each microparticle is composed of a matrix of crosslinked polyanionic polymer filaments, said matrix being capable of contracting from a swollen, decondensed phase to a condensed, partially dehydrated phase in the presence of multivalent cations having at least two positive charges, said adding being carried out in the presence of a concentration of monovalent cations that maintain the microparticles in their swollen, decondensed state, whereby said therapeutic compound becomes infused into the microparticle matrices, after said therapeutic compound has infused into the decondensed microparticles, adding multivalent cations to the medium at a concentration effective to fully condense the microparticles, thereby forming an aqueous suspension of condensed-phase microparticles having entrapped therapeutic compound, and treating the condensed-phase microparticles for storage in a desired storage state.

2. The method of claim 1, wherein said treating comprises washing the condensed-phase microparticles for storage in an aqueous suspension.

3. The method of claim 1, wherein said treating comprised removing suspension medium, for storing the condensed-phase microparticles in a partially hydrated state.

4. The method of claim 1, wherein sad entrapped therapeutic compound is present in the suspension at a concentration which is greater than its water solubility in the aqueous medium forming the suspension.

5. The method of claim 1, wherein said therapeutic compound is a polypeptide.

6. The method of claim 1, wherein the polymer filaments forming the microparticle matrix are selected from the group consisting of sulfated, sulfonated, carboxylated, and polyphosphated polyanionic polymers, and said therapeutic compound is cationic at the pH of the suspension medium.

* * * * *